US012763213B1

(12) United States Patent
Saxena et al.

(10) Patent No.: US 12,763,213 B1
(45) Date of Patent: Oct. 13, 2026

(54) DETERMINING PATIENT STATE AND NEXT-BEST ACTIONS WITH THERAPEUTIC INTERVENTIONS

(71) Applicant: Evidium, Inc., San Francisco, CA (US)

(72) Inventors: Arnav Saxena, San Francisco, CA (US); Wian Stipp, San Francisco, CA (US); Matthew Mcsorley, Pittsburgh, PA (US); Fady Nakhla, San Francisco, CA (US); Sean Thomas, San Francisco, CA (US); Carl Bate, San Francisco, CA (US)

(73) Assignee: Evidium, Inc., San Francisco, CA (US)

( * ) Notice: Subject to any disclaimer, the term of this patent is extended or adjusted under 35 U.S.C. 154(b) by 0 days.

(21) Appl. No.: 19/189,664

(22) Filed: Apr. 25, 2025

Related U.S. Application Data

(60) Provisional application No. 63/789,664, filed on Apr. 16, 2025.

(51) Int. Cl.

| | |
|---|---|
| ***G16H 50/20*** | (2018.01) |
| ***G06N 5/02*** | (2023.01) |
| ***G16H 10/60*** | (2018.01) |
| ***G16H 50/30*** | (2018.01) |

(52) U.S. Cl.
CPC ............... *G16H 50/20* (2018.01); *G06N 5/02* (2013.01); *G16H 10/60* (2018.01); *G16H 50/30* (2018.01)

(58) Field of Classification Search
CPC ......... G16H 50/30; G16H 10/60; G16H 50/20
See application file for complete search history.

(56) References Cited

U.S. PATENT DOCUMENTS

| | | | | |
|---|---|---|---|---|
| 11,869,674 | B2 * | 1/2024 | Tulley | G06F 40/279 |
| 12,300,392 | B2 * | 5/2025 | Bate | G06F 40/279 |
| 2019/0198172 | A1 * | 6/2019 | Nelson, Jr. | G16H 50/30 |
| 2020/0159848 | A1 | 5/2020 | Yeo | |

(Continued)

OTHER PUBLICATIONS

Saqi et al. 2019, "Navigating the disease landscape: knowledge representations for contextualizing molecular signatures," Brief Bioinformatics, Mar. 25, 2019;20(2);609-623. Doi; 10.1093/bib/bby025. PMID: 29684165; PMCID: PMC6556902.

(Continued)

*Primary Examiner* — Jay M. Patel
(74) *Attorney, Agent, or Firm* — Beyer Law Group LLP

(57) ABSTRACT

A computational evidence platform extracts clinical concepts from medical evidence sources and creates a knowledge graph of elemental factors, investigations and therapeutic interventions (drug and nondrug therapies) all linked to medical conditions. Condition-dependent properties are stored between medical condition nodes and these factor, investigation and therapeutic intervention nodes. The knowledge graph is queried using natural language from a user interface, API or AI agent with contextual patient data or without. A document indexer creates elemental nodes from a document and a document node and stores these in the knowledge graph. A patient state is determined by extracting factors, investigations and therapies from a patient chart. Next-best actions per condition are determined by identifying factors, investigations and therapies not yet performed. Next-best actions across conditions are determined by assuming that therapies not present are now present in a patient chart.

22 Claims, 18 Drawing Sheets

(56) References Cited

U.S. PATENT DOCUMENTS

| | | | |
|---|---|---|---|
| 2020/0242349 | A1 | 7/2020 | Ferreira Moreno et al. |
| 2022/0059224 | A1* | 2/2022 | Tulley .................... G10L 15/26 |
| 2022/0300713 | A1 | 9/2022 | Gnanasambandam et al. |
| 2022/0310264 | A1 | 9/2022 | Kaput et al. |
| 2022/0375622 | A1 | 11/2022 | Gnanasambandam et al. |
| 2023/0282368 | A1 | 9/2023 | Josephson et al. |
| 2023/0335299 | A1* | 10/2023 | Tulley .................. G06F 40/279 |
| 2024/0153648 | A1 | 5/2024 | Bate et al. |
| 2024/0290435 | A1 | 8/2024 | Desai |
| 2025/0253061 | A1 | 8/2025 | Bate et al. |
| 2025/0253062 | A1 | 8/2025 | Bate et al. |

OTHER PUBLICATIONS

Timilsina et al. 2023, “Knowledge Graphs, Clinical Trials, Dataspace, and AI: Uniting for Progressive Healthcare Innovation. ”2023 IEEE International Conference on Big Data (BigData), Sorrento, Italy, 2023, pp. 4997-5006, DOI: 10.1109/BigData59044.2023.10386401.

* cited by examiner

DETERMINING PATIENT STATE AND NEXT-BEST ACTIONS WITH THERAPEUTIC INTERVENTIONS

CROSS-REFERENCE TO RELATED APPLICATIONS

This application claims priority of U.S. provisional patent application No. 63/789,664, filed Apr. 16, 2025 entitled "Computational Evidence with Therapeutic Interventions and Applications Thereof", which is hereby incorporated by reference. This application also incorporates by reference U.S. Pat. No. 11,869,674, titled "Translation of Medical Evidence into Computational Evidence and Applications Thereof."

FIELD OF THE INVENTION

The present invention relates generally to the use of medical evidence. More specifically, the present invention relates to therapeutic interventions that are made computational.

BACKGROUND OF THE INVENTION

Currently, U.S. healthcare waste is estimated at $1.5 T, and a number of reasons are evident. For one, bias and misdiagnosis are omnipresent, with each of us likely to be misdiagnosed in our lifetime or impacted groups due to bias, and the timeframe for new research to be put into practice is 5-17 years. Further, there is already more knowledge than is humanly possible to stay current on and apply, and only 20% of clinical guidelines are backed by high-quality evidence.

Unfortunately, the burden to be more efficient falls on clinicians, who have reached a ~50% burnout rate. Even though evidence is the fundamental unit of diagnosis, treatment, payer economics, research and regulation, current scientific practice and operational medical knowledge is primarily represented separately as documents and in if-then rules in workflows. This severely limits diffusion, feedback and scalability. And, while powerful, AI architectures based on text alone are not sufficient to represent, process or reason on this knowledge controllably or reliably.

Physician and healthcare needs for evidence and guidance are at an inflection point. Solving this problem is critical to improved (and improving) health outcomes and sustainable healthcare. Current content providers, i.e. publishers, such as DynaMed, BMJ, UpToDate, etc., provide encyclopedia-style medical content look-up for clinicians covering diagnosis, treatment and management of diseases. They assemble the published evidence through expert, human-centric activity—looking at published papers, sometimes supported by tooling to help human-led assembly activity. These papers are supporting references only. Current best practice takes what are essentially narrative paper documents, even if they are in a digital form, and boils them down to other documents, again in narrative form, that require human beings to interpret their contents. This process is slow, inefficient and generalized, although it is the best available, until now.

Medical evidence is the fundamental form of knowledge underpinning the science and practice of medicine. It is used in the understanding, prevention, treatment and diagnosis of disease. There is no effective way, however, to diffuse, obtain feedback or strengthen evidence across the system. Today, evidence is predominantly narrative and document-based for dissemination. This creates significant problems including: delay—there is a 3- to 19-year lag from bench to bedside; ineffective at scale—manual search is a time-sink in practice; alert fatigue—documents become hard coded rules out of context; and minimal feedback—there is sparse feedback from practice back to research. Further, there is a tendency to put medical evidence into "silos," i.e., treatments and other therapeutic interventions may be described separately from diagnostic factors of medical conditions and separately from investigations used for diagnosis. There is no overarching framework for medical reasoning that can make use of all relevant medical evidence in a computationally efficient manner.

Accordingly, a new platform, architecture and techniques are needed to address the above deficiencies.

SUMMARY OF THE INVENTION

To achieve the foregoing, and in accordance with the purpose of the present invention, a knowledge graph is disclosed that includes elemental diagnostic and risk factors, diagnostic investigations, and elemental therapeutic interventions, all made computational to provide answers to any medical question.

In a first embodiment, a medical query is executed upon a knowledge graph that includes elemental therapeutic interventions.

In a second embodiment, a method indexes a document and stores its elements and a document node in a knowledge graph.

In third, fourth and fifth embodiments, a medical query is executed upon a knowledge graph with document indexing that may include elemental therapeutic interventions, elemental diagnostic factors and elemental diagnostic investigations.

In a sixth embodiment, a patient state is determined using the knowledge graph.

In a seventh embodiment, next-best actions for a medical condition are determined using a knowledge graph.

In an eighth embodiment, next-best actions across medical conditions are determined during diagnosis and may include an elemental therapeutic intervention.

In a ninth embodiment, next-best actions across medical conditions are determined during treatment and may include an elemental therapeutic intervention.

In tenth and eleventh embodiments, therapeutic interventions in a medical evidence source are translated into computational elements.

Advantageously, a knowledge graph with the elemental concepts of diagnostic and risk factors, investigations and therapeutic interventions now connects different ontologies, i.e., factors connect to SNOWMED, investigations connect to LOINC, and interventions connect to RxNorm, FDB, etc. A knowledge graph with connected ontologies is more powerful and has greater computational ability.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

It is realized that multiple clinical ontologies and taxonomies exist (e.g. SNOMED-CT), but that these by themselves do not provide the end-to-end computational representation necessary to make medical evidence operational or computational. A given taxonomy can only perform limited reasoning: while one taxonomy provides a hierarchy of diagnostic factors and another taxonomy provides a hierarchy of conditions, each provides no information as to how particular factors relate to a condition, how a diagnosis of a patient may be derived using these hierarchies, or how treatments may be used to perform reasoning. These are hierarchies of concepts, not relationships, and cannot be used to perform reasoning to link a condition to particular diagnostic factors, to link factors and investigations to treatments, or to link treatments to possible conditions.

We represent medical evidence, the "raw material," as computational evidence that is application ready, computational, diffusible and deployable at unprecedented scale and associated utility across healthcare stakeholders. Computational means that the medical evidence (conditions, factors, investigations and treatments), relating to the understanding of, diagnosis of and treatment of medical conditions, is processable by software applications (including artificial intelligence and other computational models), and combinable with other healthcare data (including patient data and other real-world data), in context and in real time.

The underlying database provides computational elements (representing conditions, factors, investigations and treatments) found in medical evidence sources in narrative form; the linking of these computational elements allows for computation using the database to provide answers to medical questions. We believe that the way to scale the delivery of quality healthcare within the world of precision medicine is to make medical evidence computational by converting it into these linked computational elements. Such computational elements can be used in real time and within the technical and cognitive workflow of the clinician and overcome deficiencies in the prior art.

Computational Platform

Figure 1:
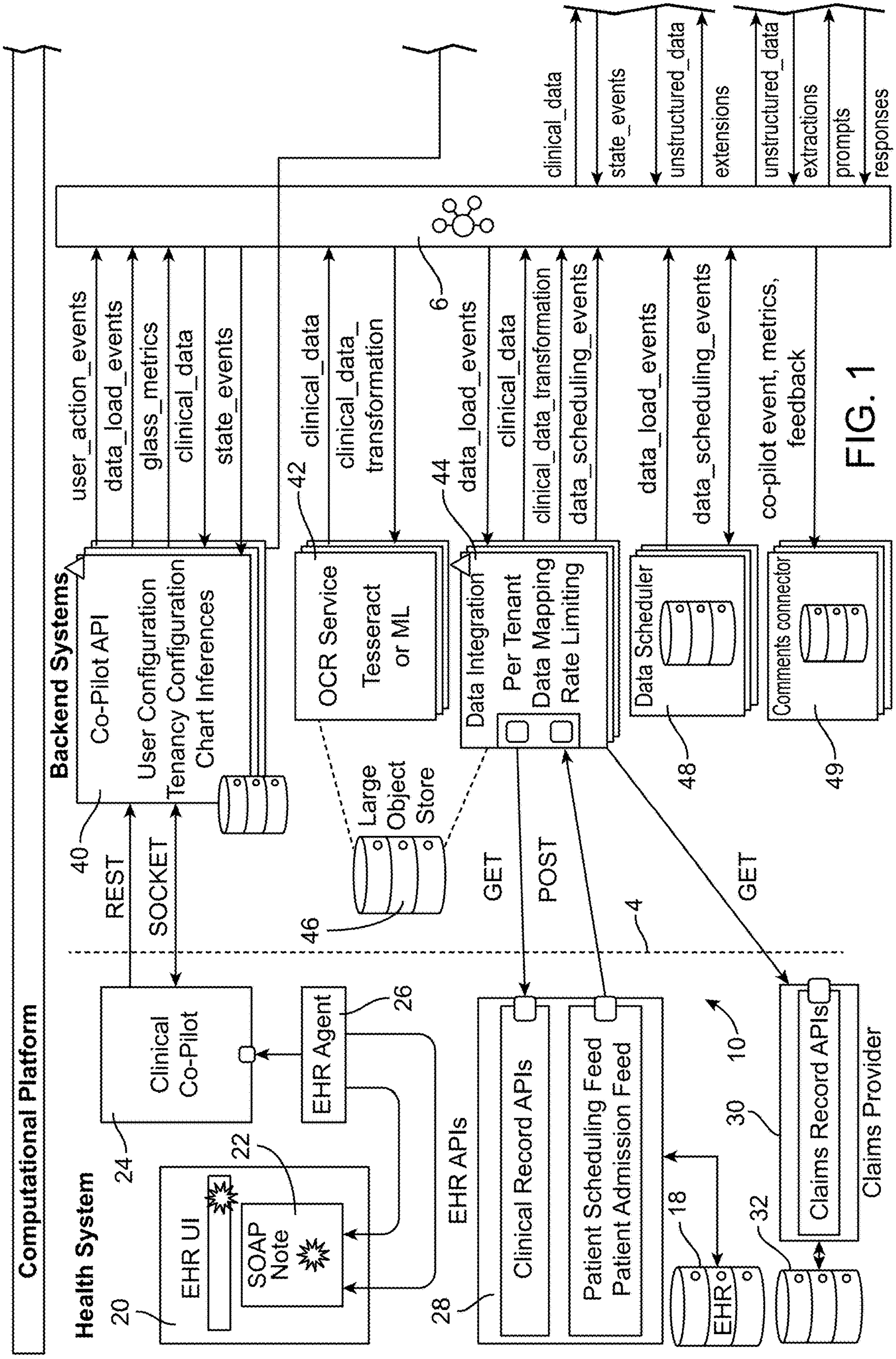
FIG. 1 illustrates a platform able to answer medical queries, diagnose a patient's condition and recommend next-best actions.
Figure 1:
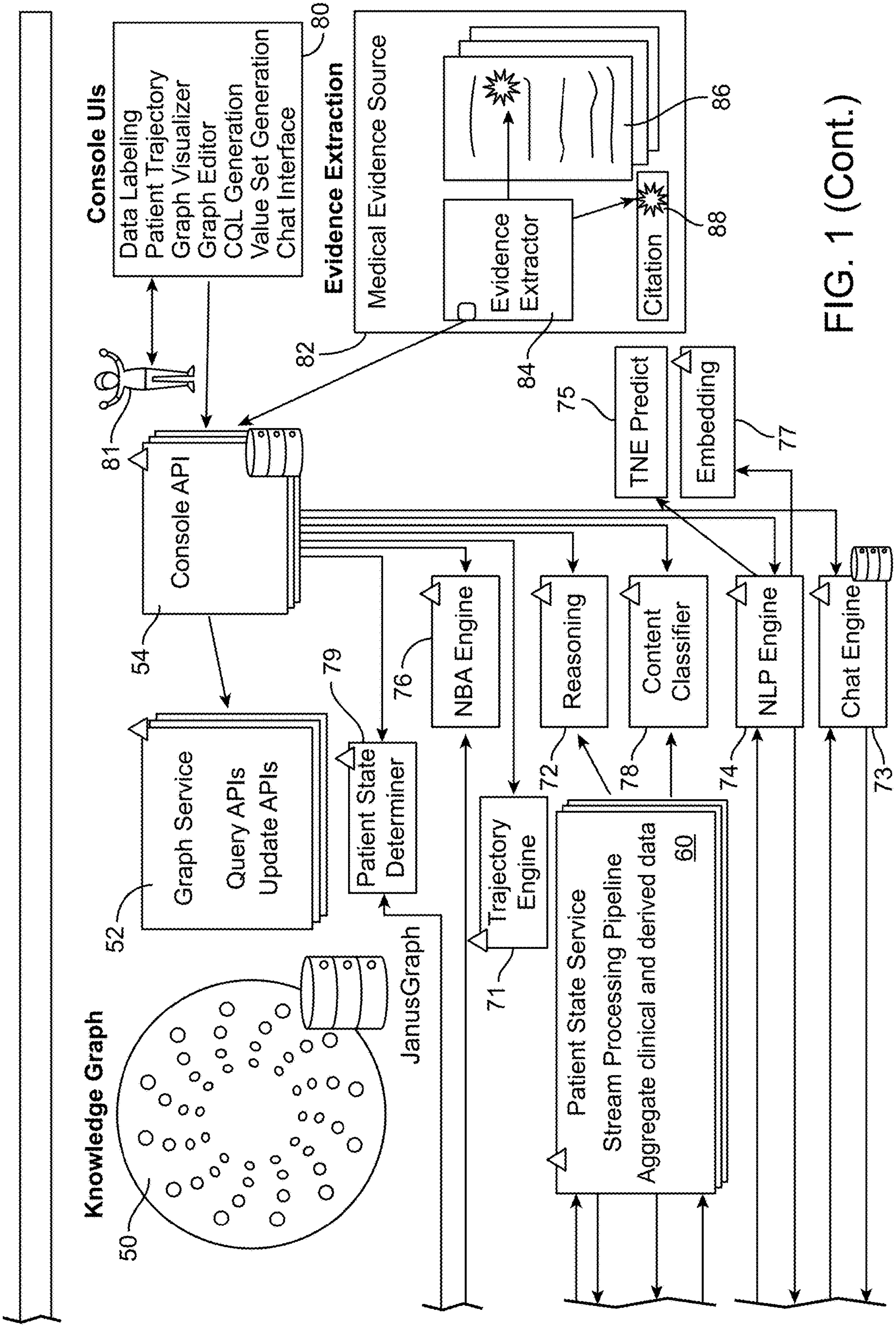

FIG. 1 illustrates a computational platform 10 able to evaluate and diagnose a patient's condition, recommend a next-best action or actions, recommend a treatment or treatments separate from or in addition to a diagnosis, perform diagnosis by treatment, among other tasks, all based upon medical evidence and medical guidelines which have been made computational. Generally, platform 10 may be viewed as including any number of health systems (the user environment) and backend systems, shown separated by vertical dashed line 4. A health system is that hardware and software generally located on customer premises (such as in hospital, clinic, doctor's office, insurance company, or other client of the platform, etc.), while the backend systems are generally that hardware and software located at offices and locations owned by or under order control of the provider of platform 10, such as locations controlled by Evidium, Inc. or located in cloud services such as AWS, Azure, Paperspace, etc. Nevertheless, certain components of the health system (such as an EHR database 18) may be located remotely from the clinician (e.g., in the cloud) and in one embodiment a user interface software application ("Clinical Co-pilot") 24 is also cloud based and accessed by a clinician using a Web browser on a computer in his or her office. Other components of a health system may also be cloud based. Note that "clinician" used herein refers to medical doctors, physicians, physician assistants, nurse practitioners and other medical professionals qualified to diagnose, treat and care for patients.

An EHR 18 (electronic health record, also referred to as an electronic medical record or EMR) system of record is an external database providing the EHR-stored medical data for the patient, including but not limited to patient demographics, symptoms, investigations, examinations, laboratory test results, signs, diagnoses, treatments or guidelines performed and history. Data may be accessed in both real time and asynchronously pre-encounter or post-encounter. Data is accessed via various methods including but not limited to FHIR (Fast Healthcare Interoperability Resources) standards.

EHR UI 20 is the user interface of the EHR system; the user interface application 24 is a stand-alone application that runs on the clinician's computer (e.g., it is a browser application), although it is capable of being launched from the EHR UI 20 environment with a single sign-on authorization including but not limited to SMART on FHIR and other relevant standards. EHR Agent 26 is an event detector that detects user actions on a computer. It sends messages via user interface 24 to the Co-pilot API 40 which in turn is responsible for retrieving the relevant information from the EHR, automatically detecting any new relevant data, including but not limited to new data added to the EHR system (for example, a new patient record or state change of patient data such as diagnostic data both in real-time and asynchronous modes of operation), and provides that data to application 24, i.e., data that is typically added by a clinician. Shown is a standard SOA P note 22 by which a clinician may enter observations of a patient during or outside of an encounter; other data entry techniques may also be used. EHR APIs 28 is a collection of APIs such as FHIR, USCDI (United States Core Data for Interoperability), CDS Hooks, and vendor-specific APIs which allow EHR agent 26, user interface 20 and other components to communicate with the EHR system. Claims record APIs 30 are any number of APIs used by a claims provider (such as a health insurance company, e.g. UnitedHealth Group, CVS Health, Elevance Health Inc.) to access platform 10 in order to submit queries to knowledge graph 50 and perform other tasks as will be described below, and which may use patient claims information from medical visits and procedures, etc. from a claims database 32.

Clinical Co-pilot 24 is a real-time, fully-automated, possibly hands-free software application and user interface, designed specifically to be the system of interaction by which a clinician may enter patient data, direct that a patient EHR be downloaded to the platform, request a diagnosis or patient state, request a next-best action, treatment, etc. of a patient either during a patient encounter or when the patient is not present, or perform any query of the knowledge graph. For example, application 24 is used by a clinician in real time during a patient encounter (live, by telephone, online via computer, chat via mobile telephone or computer, a video call, etc.) or may be used by a clinician before or after a patient encounter. Application 24 is an interface to any of the backend engines herein which run in parallel with the clinician's actions and do not require any additional input from the clinician. Application 24 may be used as an overlay, as a window tab, or may appear using other user interface techniques.

Application 24 accepts manual clinician entries and selections (e.g., typed input, mouse input, etc.,) and may use speech recognition technology (microphone and speech recognition software not shown) as well as live note capture technology to collect real-time patient encounter information. Any verbatim text (either from manual data entry, speech recognition, live notes, from the patient EHR medical chart, etc.) is then converted in real time into factors, investigations, treatments, prior conditions, history, etc., by NLP Engine 74 and matched to nodes in knowledge graph 50 for use by NBA engine 76, Trajectory Engine 71, Reasoning 72, Content Classifier 78, Determiner 79 and Chat Engine 73 to determine patient state, potential patient conditions, next-best actions, treatments, etc. Application 24 is able to display pertinent positive and negative history from the patient's medical chart in the EHR system that has been extracted by NLP Engine 74 and Reasoning 72.

In one embodiment, application 24 is an application integrated into the EHR environment via relevant standards such as a SMART (Substitutable Medical Applications, Reusable Technologies) on FHIR application for EHRs (such as Epic and Cerner), and is integrated into the clinical workflow. In another embodiment, application 24 is a standalone system, integrated with relevant external data sources. The suggestions from application 24 are provided for expert consideration and not as a replacement for the clinician. Thus, application 24 provides real-time (or outside of a patient encounter), in-context differential diagnosis, next-best-action and treatment suggestions to validate and expand clinical consideration, along with query capability.

OCR Service 42 provides mechanisms to convert images of text to digital text strings for further analysis. Data Integration Service 44 mediates access to external EHR services including the translation from the abstract data model used by the CEP to the specific data models of the EHRs. Data Scheduler Service 48 provides a mechanism that enables patient charts to be analyzed and cached prior to a patient's visit thus facilitating better real-time performance. Comments Connector 49 is a software module that collects user feedback for different systems that can be present in the form of reviews, upvote and downvote ratings, and other similar mechanisms. Communications channel 6 is a software layer that communicates information between application API 40 (and Comments Connector 49 and components 42, 44, 48, 49) with components 60, 74, 76 and 73.

Knowledge graph 50 is a database or data store that stores the extracted information from the medical evidence sources after that information has been translated into computational elements. Knowledge graph 50 may also be referred to as a clinical knowledge graph, a database, a knowledge base, an evidence base, or an inferential database. Any of a wide variety of types of databases or data stores may be used to store this information such as a relational database, an object store, an object-oriented database or non-relational database (NoSQL). In one embodiment, knowledge graph 50 is implemented using a JanusGraph graph database having nodes and arcs (or links), the nodes containing medical evidence of different types (e.g., conditions, differential diagnoses, diagnostic factors, risk factors, investigations, treatments) and the arcs (or links) indicating linkages, causality, flow, or other (made clear by the context) between the nodes. Depending upon the context, these arcs or links may be unidirectional or bi-directional. In one particular embodiment, the knowledge graph is undirected and thus allows traversal in any direction depending upon the use case. For instance, while predicting conditions given a set of investigation results and diagnostic factors, we can traverse up from EDIs and EDFs to condition nodes, whereas if a user wishes to find all diagnostic factors of a particular condition, we can traverse down from condition nodes to EDFs. Further, the knowledge graph may contain nodes and edges, and the edges themselves may also hold any of the medical evidence listed above or properties of nodes.

Evidence extraction 82 is performed to extract textual medical evidence from any of a variety of sources for representation within the knowledge graph 50. Any of a wide variety of medical evidence sources 86 may be used and include: National Library of Medicine; JAMA Rational Clinical Evidence; BMJ Best Practice (or other British Medical Journal databases); SNOMED-CT (Systemized Nomenclature of Medicine-Clinical Terms); LOINC (Logical Observation Identifiers, Names, and Codes) database; CPT (Current Procedural Terminology) codes; StatPearls content; and other online sources such as Merck Manuals, WebMD, NORD (raredisease.org), the CDC (for endemic information), the WHO, RxNorm (for medications), First Data Bank (FDB, for drug-drug interactions), NICE and other accredited associations that publish treatment guidelines such as American College of Cardiology etc.; as well as laboratory test reference ranges, drug interactions (drug-drug, drug-condition, drug-food), clinical dictionaries, and content on rare diseases. The evidence extractor 84 can extract clinical items from any textual data source; it maps extracted concepts to these code systems or ontologies.

Typically, the sources used are in electronic form, such as a JSON file, XML file, or other electronic format representing textual information. If they are Web sites, then they may be marked up in HTML. The textual information may be free-form text, may be in narrative form, may be semi-structured text (e.g., text within flow diagrams, decision trees, etc.). In addition, evidence-based medicine sources are used and include a collection of external data, such as datasets of clinical support reference content for healthcare professionals which contain best practices, evidence-based research relevant for clinical decision support including diagnosis and treatment.

An evidence extractor 84 is a system which extracts relevant text from an evidence source and delivers it to NLP engine 74 for recognition of the clinical concepts within the text. Evidence extractor 84 identifies and retrieves appropriate clinical data from evidence sources discussed above and delivers this data to any component requiring clinical concept validation. By surfacing authoritative medical evidence that supports system decisions, it helps build user confidence in the system's recommendations while also providing explanation directly from the evidence source.

The extractor facilitates the selection, extraction, and delivery of relevant text to the NLP engine 74 for the recognition of domain-specific concepts. By way of example, when text related to a particular medical condition is input the extractor extracts the condition, its diagnostic factors, risk factors, investigations, any differential diagnoses, rankings, treatments, etc. and delivers those to the NLP engine. The extractor 84 also extracts a citation or citations 88 associated with the extracted text. The extractor may be implemented in forms such as a stand-alone application or a Web browser plug-in function. After the NLP engine extracts structured concepts from unstructured or narrative text, the evidence extractor fetches the appropriate condition, its diagnostic factors, risk factors, investigations, any differential diagnoses, rankings, treatments, etc. associated with the structured concepts.

The extractor also allows users to author custom evidence of their own. An example use case is a medical association that publishes treatments for conditions; the association can use the Graph Editor tool to build new computational treatment nodes and annotate them with their custom evidence. Use of an NLP engine for evidence extraction is optional, for example when the extracted text is already in structured form or when a human-in-the-loop reviews and edits the extracted text in order to place it into structured form.

Console user interface (or interfaces) 80 is used by a person 81 and includes a Graph Visualizer for viewing knowledge graph 50, a Graph Editor by which the person views or reviews information extracted from the medical evidence, corrects errors, adds factors (or other nodes), perform groupings, etc., thus changing and improving the extracted evidence before it is stored into knowledge graph 50. A CQL Generation interface allows the user to generate executable CQL (or other) code by providing natural language descriptions of any custom query the user wishes to execute on a patient database. A Value Set Generation interface allows a user to generate value sets of any desired elements of the knowledge graph. A Chat Interface allows the user to query the knowledge graph in natural language (e.g., via an LLM) and retrieve context-relevant clinical information along with evidence. A Patient Trajectory interface allows the user to find potential future trajectories of a patient along with analyses of risk scores and evidence that explain the predicted trajectories.

NLP (natural language processing) engine 74 may include any number of NLP processes (such as an NLP pipeline) and each may use a model or not. The NLP processes that may be used include but are not limited to: Word Segmenter, Sentence Segmenter, Negation Cues, Negation Scopes, NER (Named Entity Recognition), Relationship Prediction, NEL (Named Entity Linking), Phrase Extractor, Composite Matcher, Embedding Matcher, Graph Matcher, NLI and Long-to-Long Matcher. The NLP engine may also include models or functions for extracting temporality cues and scopes, experiencer cues and scopes, sex cues and scopes, and age cues and scopes. Preferably, the NLP engine is trained in the domain of medical concepts. NLP engine 74 is used not only for extracting information from medical evidence sources, but also for interpreting a patient's chart and outputting diagnostic factors, risk factors, investigations, results of investigations, treatments and other items of a patient's medical history that may be matched to nodes within the knowledge graph or used to implement a diagnosis, next-best action, treatment or other query within the course of traversing the knowledge graph.

NBA engine 76, Reasoning service 72, Content Classifier 78, Chat Engine 73, Determiner 79 and Trajectory Engine 71 are all software modules used by platform 10 to perform various tasks. Patient State Service 60 functions as an interface layer that ingests patient data from diverse sources and in diverse format (e.g., FHIR records from an EHR, patient data input from application 24, claims information from insurance providers). It transforms this heterogeneous data into system-specific representations tailored to the internal requirements of the software modules used (e.g. 71-73, 76, 78, 79). Patient State Service 60 also acts as a caching layer that serves to enhance real-time operation for already-analyzed patients and to control access to the various functions provided by the platform. By way of example, during a diagnosis, a next-best action or other query, patient state service 60 keeps track of the patient's state (including the factors, investigations, treatments, etc. that the patient has presented with over time or that are presented in the encounter). Patient state service 60 may also send the patient state (including any inferred factors, investigations, treatments from the Reasoning service) to the Content Classifier 78 (or other diagnostic classifier) which performs a straight classification using condition scoring.

During determination of the patient state, service 60 takes the known factors, treatments and investigations and sends those to reasoning service 72 in order to infer other factors, treatments and investigations using an ontology link in the corresponding EDF, ETI or EDI. Using the appropriate ontology, service 72 and walks the relevant ancestor-descendant chains. Reasoning service 72 also understands the ancestor-descendant relationships of clinical tests, e.g. CBC with differential is a parent of CBC (complete blood count) is a parent of Hematocrit and White Blood Count.

For example, given that the patient has "acute fever" we may also infer that the patient has the broader factors "fever" and "change in body temperature." Not all conditions are described in the literature with the same level of specificity, and similarly, patients may be very specific in their description of symptoms, e.g. a patient suffering from botulism might report very specific left upper quadrant abdominal pain, whereas the evidence for botulism does not localize the abdominal pain to a specific area and its diagnostic factor is "abdominal pain" only. Without the inference from LUQ abdominal pain to UQ abdominal pain to "abdominal pain," a diagnostic factor for botulism would be missed.

Chat Engine 73 performs dynamic conversation orchestration against an input medical query from a clinician with optional additional context as can be fetched from service 60 or supplemental database integrations. It responds by executing appropriate reasoning sequences, including calling NBA Engine, Reasoning, Determiner and NLP Engine where required to return an answer grounded in the contents of the knowledge graph. TNE Predict module 75 performs temporality, negation and experiencer attribute tagging on elements of the knowledge graph. Embedding module 77 transforms medical concepts (factors, diagnoses, investigations, procedures, treatments, etc.) into dense vector representations in a high-dimensional space. These embeddings capture semantic relationships between medical concepts, enabling efficient similarity-based retrieval. Trajectory Engine 71 is used by an insurance company (or other) to traverse a patient trajectory in a guideline using patient claims data. Modules 40, 44, 52, 54, 60, 71-74 and 76-79 (flagged with a small triangle) generate responses based upon clinical data structured in the knowledge graph, ensuring semantic consistency, factual accuracy, and contextual relevance across all system operations.

Computational Elements

In general, the platform makes medical evidence computational including medical conditions, factors, investigations (including laboratory tests and examinations) and therapeutic interventions (i.e., drug and nondrug treatments). A medical condition may be any condition, a disease, an orthopedic anomaly, an adverse drug reaction, or a drug-to-drug interaction.

A diagnostic factor is a factor that the physician can observe, detect or measure quickly or have the patient describe to him or her during an office visit (traditional signs and symptoms), while an investigation is a laboratory test or an examination performed by a specialist; both are more sophisticated and take more time. By way of example, diagnostic factors include: "patient has a headache," "patient skin appears yellow," "patient reflexes appear normal," etc. Thus, the value of a particular diagnostic factor may be a simple yes or no, a numerical value, a numerical range, the presence or absence of the diagnostic factor, an observation (e.g., "appears normal"), or other results such as a specific physiological description like "the nasopharynx is symmetric." The platform also distinguishes between diagnostic factors and risk factors; as is known in the art, a diagnostic factor is caused by a condition, whereas a risk factor may contribute to, or partially cause, a condition. Risk factors may include gender, age, family history, smoking, medications, etc., and examples include: "sex is male," "patient smokes," and "family has a history of colon cancer."

Typically, investigations require either the collection and processing of some sort of biological sample (a laboratory test) or a physiological analysis using some sort of device (an examination). Laboratory tests may include fluid analysis (e.g., blood panel, urine, semen, and CSF), and examinations may include diagnostic imaging (CT, MRI, X-ray, PET, ultrasound, endoscopy) and pathology analysis among others. By way of example, the result of a laboratory test is "CBC blood test shows reduced hemoglobin level" and the result of an examination is "MRI of the pelvis appears normal." Thus, the result of a particular laboratory test or examination may be a simple yes or no, a numerical value, a numerical range, the presence or absence of a particular item, an observation (e.g., "appears normal"), or other result. Depending upon the implementation, vital signs, e.g. heart rate, blood pressure, oxygen saturation, etc. may also be considered as investigations—they can be performed quickly, by clinicians with a lower level of education or training, and for little to no cost. Generally, although not always, investigations will be the ones with numbers or numeric ranges as results whereas diagnostic factors indicate the presence or absence of something. Some observable factors may be considered investigations.

Our design uses EDFs (elemental diagnostic factors) to represent factors, which are computational elements resulting from translating human-readable evidence. Clinical factors described by evidence-based medicine and medical guidelines are translated into EDFs. Specifically, an EDF is a clinical factor that may be evident in a number of conditions, either as caused by a condition (e.g., signs, symptoms, vital signs) or as a risk factor that may contribute to the cause of a condition. Traditional evidence-based medicine considers factors on a condition-by-condition basis; EDFs enable these factors to be disambiguated across conditions by the platform. In cases where the same factor applies to multiple conditions (but may be referred to by different terminology), EDFs enable those like factors to be understood as having the same meaning. Thus, EDFs provide a common representation of a potential disease state of a patient, useful in diagnosis as well as in next actions and treatment. As an example, EDFs disambiguate clinical factors where one human-readable text describes "neck stiffness" for one condition and "nuchal rigidity" for another; the EDF "stiff neck" replaces both, thus using a single EDF across both conditions. Another factor is possibly described in different sources as "being feverish" or "high temperature," all meaning the same; thus the single EDF "fever" is used.

EDFs may also be used to describe higher-level factors than the atomic elements, for example the factor group "GI symptoms" is defined to include the EDFs "nausea," "abdominal pain" and "vomiting." Another example is the factor group "constitutional symptoms," defined using the EDFs "fever," "malaise," and "weakness." Another example is a medical reference that lists the diagnostic factor "pelvic pain" under the condition "ectopic pregnancy." The factor "pelvic pain" is quite broad and we extract from the narrative in the reference the very specific EDFs of "acute pelvic pain," "right-lower quadrant pain," "lower abdominal pain," and "pelvic pain" which then allows "pelvic pain" to be a factor group and used for other conditions (e.g., BPH, benign prostatic hyperplasia which is a male condition). The following EDFs related to pelvic pain may be used: acute pp, burning pp, chronic female pp, chronic pp without obvious pathology, constant pp, cyclic pp, dull pp, female pp, hx (history) of chronic female pp, hx of cyclic pp, intermittent pp, no female pp, no pp, pp on penetration, sharp pp, throbbing pp, which are all distinct concepts used in various conditions, each being disambiguated across conditions in the knowledge graph.

EDFs are computational elements in a knowledge graph, which includes other relevant elements related to conditions, investigations and therapeutic interventions. Each EDF is applicable across multiple conditions and may be used in any computation such as diagnosis, next-best action, treatment, or other query. Each EDF is also linked to an ontology or taxonomy, including but not limited to SNOMED to allow inferences to be drawn (using reasoning service 72) and to provide standardized synonyms. A particular EDF may be found in a one-to-one relationship with another clinical factor in an ontology or taxonomy, although many EDFs are created anew and do not exist in other ontologies or taxonomies.

Each EDF may also be associated with a variety of properties specific to a particular condition such as an age and sex restriction (e.g., the factor is only applicable to persons of a particular age and only to male or female patients). These condition-specific properties may be held in a demographics node as shown below (or on an edge between the condition and the EDF) but separate from the EDF. Other conditions having that EDF may have different demographics nodes that are specific to that condition, and demographic nodes need not be present for a condition. Thus, EDFs remain elemental, independent, and can be used computationally across conditions. EDFs may also have properties defined such as temporality of the factor (historic or present), experiencer of the factor (patient or family member) and negation (whether the clinical factor does not occur or is not present). Synonyms may also be defined in an EDF and allow the EDF to be recognized across different sources that use different terms.

EDFs are made independent by placing various properties that are specific to different conditions into different data structures linked to both a particular EDF and to the particular condition. In this manner, an EDF remains independent and may be used computationally across different conditions, yet within the context of a particular condition these properties are taken into consideration. In one particular embodiment, properties of an EDF relevant to a specific condition are held in a factor group linked to that specific condition and to the EDF (or held on an edge between the condition and EDF).

Clinical factors of the patient state (from the EHR or other input source) are translated and matched to the relevant EDF in the course of diagnosis, next-best-action, treatment, or other query. This enables the clinical state of the patient to be determined, for next-best-actions to be determined, and for diagnosis and other computations to be performed across all conditions, all using the same knowledge graph.

In a similar manner, the platform uses elemental diagnostic investigations (EDIs) to represent independent laboratory tests and examinations which may be used for computation across conditions in a knowledge graph. Similar to EDFs, certain properties of a laboratory test (e.g., a result, units, range, etc.) specific to a particular condition are not held within the EDI itself (thus ensuring its independence) but are held separately (in a results node, or on an edge) yet still linked to a specific condition. Further, an investigation group specific to a particular condition represents any number of laboratory tests or examinations and has its own properties defined as well. As with EDFs, condition-specific properties are not present within the EDI, but are held in a results node, in an investigation group node, or on any edge or edges between a condition and the EDI.

And further, the platform uses elemental therapeutic interventions (ETIs) to represent independent pharmacological (drug) and nondrug therapies (or treatments) also used for computation across conditions in a knowledge graph. Certain properties of a therapeutic intervention specific to a particular condition are not held within the ETI itself (thus ensuring its independence) but are held separately (in related nodes, or on an edge) yet still linked to a specific condition. A therapy group specific to a particular condition represents any number of therapies and has its own properties defined as well. Thus, condition-specific properties are not present within the ETI, but are held in related nodes or on any edge or edges between a condition and the ETI.

Each EDF, EDI or ETI includes a link to its corresponding entry in a suitable ontology for uniquely identifying the node, performing inferences, finding synonyms, matching, etc. Embodiments may use a clinical ontology with pre-coordinated and post-coordinated expressions from SNOMED for EDFs, use logical observation identifiers names and codes (LOINC) for EDIs, use RxNorm or FDB for ETIs (pharmaceuticals), use ICD or CPT, or use UMLS or OMOP for reasoning (these last two contain crosswalks from one ontology to another). Certain nondrug therapy ETIs can also link to SNOMED, e.g., ETIs for genetic and cellular therapy can link to body structure and substance hierarchies in SNOMED. Other ETIs link to other suitable ontologies.

Each of these EDFs, EDIs and ETIs have characteristics that differentiate them from the prior art. Each is atomic: EDFs, ETIs and EDIs can represent the most specific fundamental elements of healthcare knowledge. Each is independent but can be placed in context: EDFs, ETIs and EDIs are independent with respect to any condition, but related contextual nodes (e.g., groups, demographics, results, restrictions) describe the dependence on, or relationship with, linked medical conditions. Each is composable into a representation in a knowledge graph: any healthcare artifact (notes, research papers, documents, queries, etc.) can be linked to multiple EDFs, ETIs and EDIs and hence can be represented as a composition of these computational elements in a knowledge graph. Each is made computational because each may be used in: deterministic reasoning (using logic built into these constructs and into the knowledge graph); traversal operations of a knowledge graph with defined edges and nodes (e.g., a query expansion by finding all contextually-related search terms); and probabilistic reasoning (group nodes include how an element is probabilistically related to a condition, hence allowing for probabilistic calculations and inferences). Because of these characteristics, each may be used horizontally across many use cases: patient state determination, next-best action recommendation, non-contextual or contextual querying of the knowledge graph, and document indexing and representation within the knowledge graph.

Example Knowledge Graph

Figure 2:
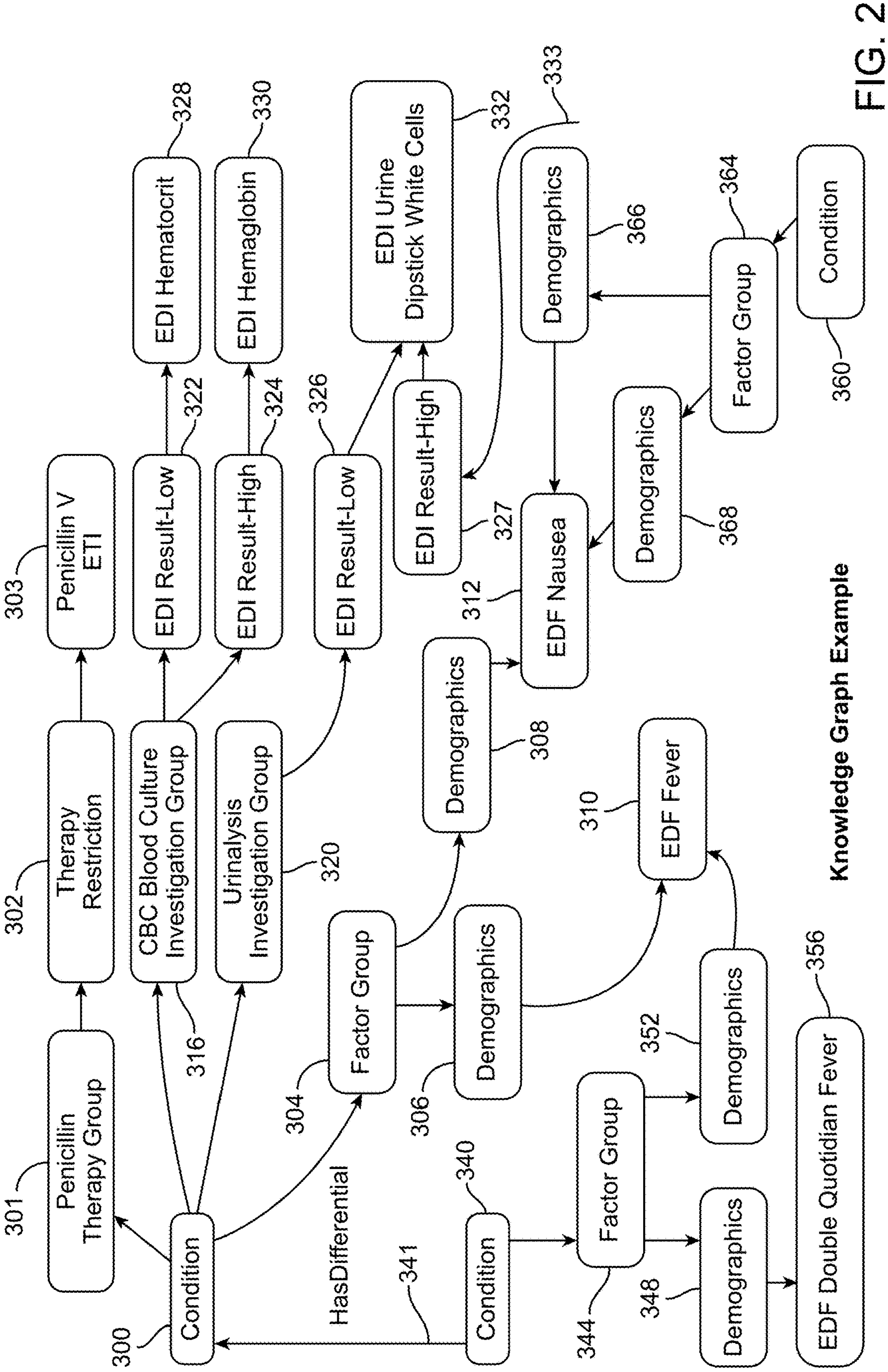
FIG. 2 an example of a visualization of a portion of a knowledge graph after medical evidence has been translated into computational elements.

FIG. 2 is a visualization of a portion of a knowledge graph after any quantity or type of medical evidence has been translated into computational elements and stored therein. Shown are specific conditions 300, 340 and 360, each having any number of factor groups, therapy groups or investigation groups. In this example conditions 300, 340 and 360 are specific medical conditions that are not named for purposes of the example. Condition 300 has a factor group 304 including two EDFs, fever 310 and nausea 312, each of those associated with a particular demographics node 306 or 308, which may be inserted automatically by the platform. Linkages between condition 300, factor group 304, demographics and EDF nodes are provided based upon information gleaned during translation of medical evidence. In this simple example, the input text revealed that the factors fever and nausea are diagnostic factors for condition 300. Similarly, linkages between condition 300 and its investigation groups, result and EDI nodes, as well as linkages between condition 300 and its therapy group nodes, therapy restriction nodes and ETI nodes are also based upon the translation of medical evidence.

Condition 340 has a factor group 344 including two EDFs, double quotidian fever 356 and fever 310, each of those associated with a particular demographics node 348 or 352. In this simple example, input text revealed that the factors double quotidian fever and just plain fever are diagnostic factors for condition 340. Note also that the EDF fever 310 is a diagnostic factor for two conditions, as is EDF nausea 312. Condition 360 has a factor group 264 including one EDF nausea 312 having a demographics node 366 and a demographics node 368. For example, there may be two demographics nodes for nausea node 312 because for this particular condition the factor is only present for the very young (node 368) or the very old (node 366). Other conditions may require two or more demographics nodes for a single EDF (or multiple Result nodes for an EDI). In another example, for the condition, "abnormal uterine bleeding," there will be two demographics nodes for the factor "women at extremes of reproductive age." One demographic node will have "females 12-19" and the other will have "females 40-60." Advantageously, each EDF has one or more demographics nodes linked to it that hold condition-dependent properties that further define how and when a particular factor is present for a specific condition. For instance, if the EDF fever 310 only occurs because of condition 300 in children under 12 years of age, that information is present within demographics 306.

Condition 340 also has a related differential diagnosis indicated via link 341 of condition 300. This means that if condition 340 is determined to be present in the patient (as described below) that a differential diagnosis is also condition 300. But, there is no corresponding differential diagnosis link from condition 300 to condition 340, thus indicating that, for this example, condition 340 is not a differential diagnosis of condition 300. Link 341 is added based upon extracting factors and investigations for a particular condition, e.g., the text may say "condition A is often mistaken for condition B." For example, influenza may be confused with RSV because they have the same signs and symptoms. Person 81 using the console will add link 341 if condition 340 might also be condition 300 but will only add a similar link from 300 to 340 if condition 340 might also be mistaken for condition 300. Such links may also be added by the platform automatically during translation by the natural language processing.

Condition 300 also has two investigation groups, CBC blood culture 316 and urinalysis 320, both also produced by portions of an evidence source being input via evidence extraction. Similar to factors, the single laboratory test EDI urine dipstick for white cells 332, is at the end of the linkage, with its possible result, EDI Result low 326, being between nodes 320 and 332. The EDI Result type of node is similar to a demographics nodes in that an EDI Result node provides a result specific to its indicated condition and is indicative of that condition only when the result has a particular value, such as "low" in node 326.

The other investigation group of condition 300 is CBC blood culture 316 and is an example of an investigation group which may include many specific tests, each having a particular value which is indicative of the condition, if that value is present. Although a CBC blood culture may include many results, only shown are the specific tests EDI hematocrit 328 and EDI hemoglobin 330, each having a particular result 322 and 324. A gain, the specific laboratory tests 328 and 330 are only indicative of condition 300 if the results 322 and 324 are as shown.

Nodes 322-326 hold the specific results of a test that indicates when condition 300 is present and EDI nodes 328-332 contain a description of the actual test itself. As with EDFs, an EDI may be linked to many different conditions, each such link including an EDI result node between the EDI and the condition, in this fashion, an EDI is independent of a condition, yet it may have a result which indicates a particular condition. By way of example, node 326 links to condition 300, and a different result node 327 of EDI node 332 with a result of "high" links 333 to a different condition (not shown). Thus, each EDI node may link to any number of EDI result nodes. Or, the result of "low" in node 326 may link to two or more different conditions, each link indicating that node 326 indicates the condition to which it is linked.

Condition 300 also links to any number of therapy group nodes, in this example to penicillin node 301 representing the penicillin class of drugs that may be used to treat this condition 300. Each therapy group node in turn links to any number of therapy restriction nodes, such as node 302, representing restrictions and contraindications for any number of ETI nodes, such as node 303, representing a specific prescribable drug (or nondrug therapy) that may be prescribed to treat condition 300. In general, restrictions inform when a particular therapy of an ETI should not be prescribed, recommended or given, or to which demographics should not be given the therapy. ETI nodes are also atomic, independent, do not include condition-dependent properties, and may be linked to any number of conditions.

Condition-dependent properties for EDFs, EDIs and ETIs are held respectively in factor group and demographics nodes, in investigation group and result nodes, and in therapy group and therapy restriction nodes. For example, each factor group node such as 304 holds a ranking indicating the likelihood that fever 310 is caused by condition 300. Separating out specific demographics and the ranking from an EDF node allows each EDF node to be truly elemental, independent and atomic in the sense that each EDF node can be referenced and used by any condition; the specifics as to how a factor manifests because of a particular condition and its ranking are held in the factor group and demographics nodes (or on edges between the condition and the EDF node), not in the EDF node. By way of example, if fever 310 presents itself in a different way for different ages depending upon whether the patient has condition 300 or condition 340, these details are held in demographics nodes 306 and 352 rather than within EDF node 310. And, because fever 310 may be ranked differently for condition 300 and condition 340, these rankings are held in nodes 304 and 344 as well. Thus, a fever 310 in the context of condition 300 is a definition of fever 310 within that node plus its properties within nodes 306 and node 304.

For certain conditions with bimodal distributions there will be two demographics nodes between fever, for example, and condition 300 (e.g., when the fever only occurs in very young children and in very old people). In another example, a patient with condition 340 may exhibit double quotidian fever 356 as well as plain fever 310, each being a separate EDF node with its own particular demographics and ranking. This separation of different fevers into different EDF nodes, each having different demographics and ranking allows more accurate diagnosis and reasoning. Because a person with condition 340 may exhibit double quotidian fever and a patient with condition 300 will not, it is advantageous to keep these two elemental factors separate yet still allow the factor "fever" to be shared by both conditions are shown.

In a similar manner, an investigations group holds a ranking for its linked EDIs, and each EDI result node holds results of the investigation specific to the condition to which it is linked. Similarly, a therapy group holds an indication ranking and the line of treatment for its linked ETIs, and a therapy restriction node includes a condition interaction for the condition to which it is linked.

Figure 3:
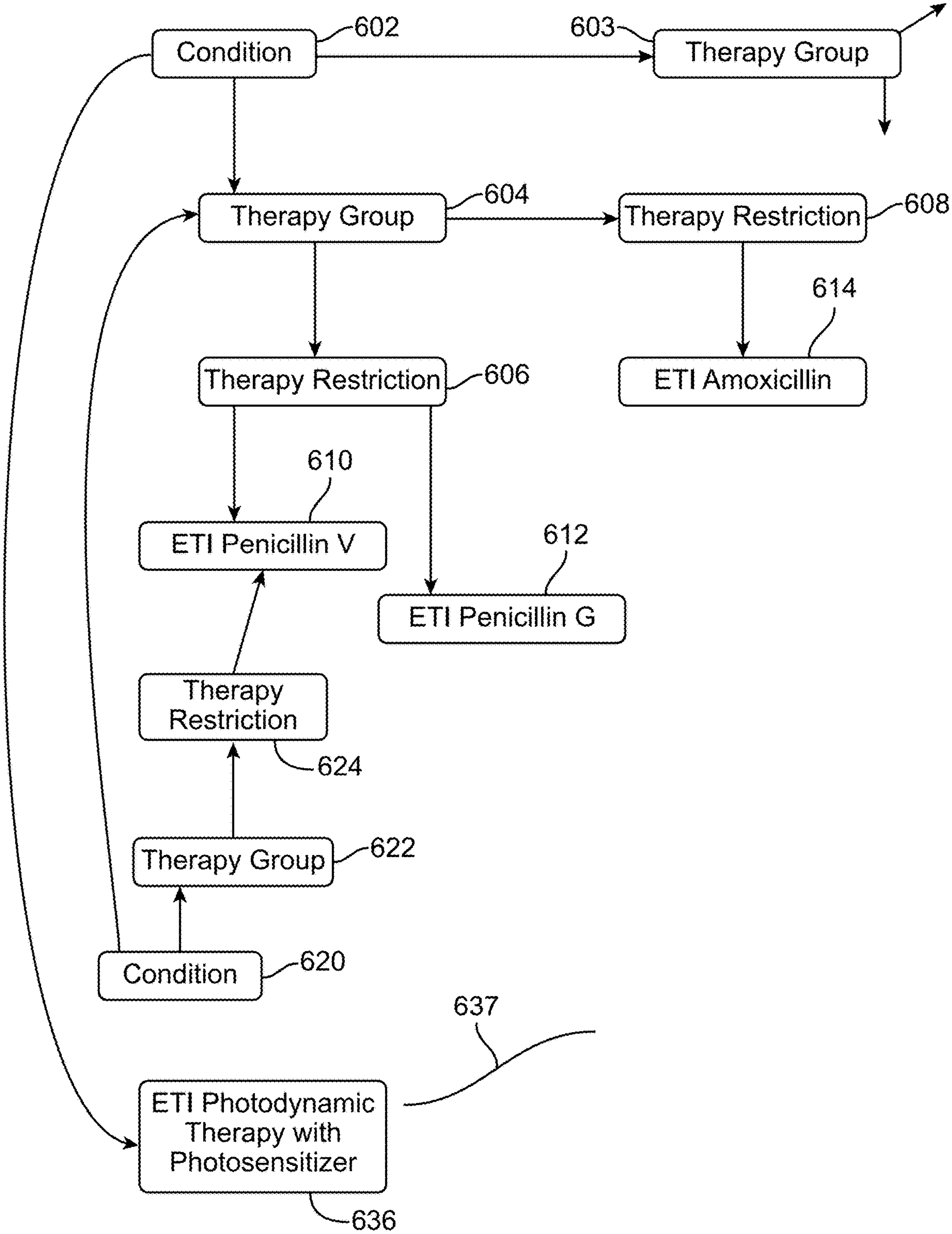
FIG. 3 is another example of a visualization of a portion of a knowledge graph that includes elemental therapeutic interventions.

FIG. 3 is another portion of a knowledge graph showing links to ETIs. Shown is a condition 602 (for example, streptococcus pharyngitis) that links to a therapy group 604, which itself links to any number of therapy restriction nodes 606, 608. The therapy group node 604 has a type such as "drug," and the name of a group of drugs that it represents such as "β-lactams." Therapy restriction node 606 includes one or more criteria indicating when the therapy represented by ETI 610 or 612 should not be used (such as an allergy or a drug-drug interaction) and may connect to any number of ETIs. Node 608 connects to ETI 614 representing the prescribable drug amoxicillin.

A particular ETI such as 610 may be linked (directly or indirectly) to any number of conditions; for any condition that suggests use of penicillin V in its particular prescribable form will have a link to ETI 610. As shown, condition 620 is linked to therapy group 604 or may be linked to ETI 610 via a different therapy group 622 and different therapy restrictions 624. For example, while therapy group 604 are "β-lactams," therapy group 622 may be "antibiotics." In this fashion, an ETI is not specific to a particular condition, does not include condition-dependent information and may be used across conditions. Condition 602 also links directly to ETI 636 which is a particular nondrug photodynamic therapy that may be used with acute strep. ETI 636 is a specific, photodynamic therapy that may be prescribed (i.e., including duration, color of light, photosensitizer chemical, etc.), and may be linked via 637 to other condition nodes that also benefit from this therapy (via a therapy restriction node and a therapy group node or directly as discussed above).

Any of the nodes described herein include a unique identifier within the knowledge graph such as a hash value (over any relevant information of the node), a universally unique identifier (UUID), a unique name, or other suitable unique identifier.

Computational Elements Detail

Figure 4:
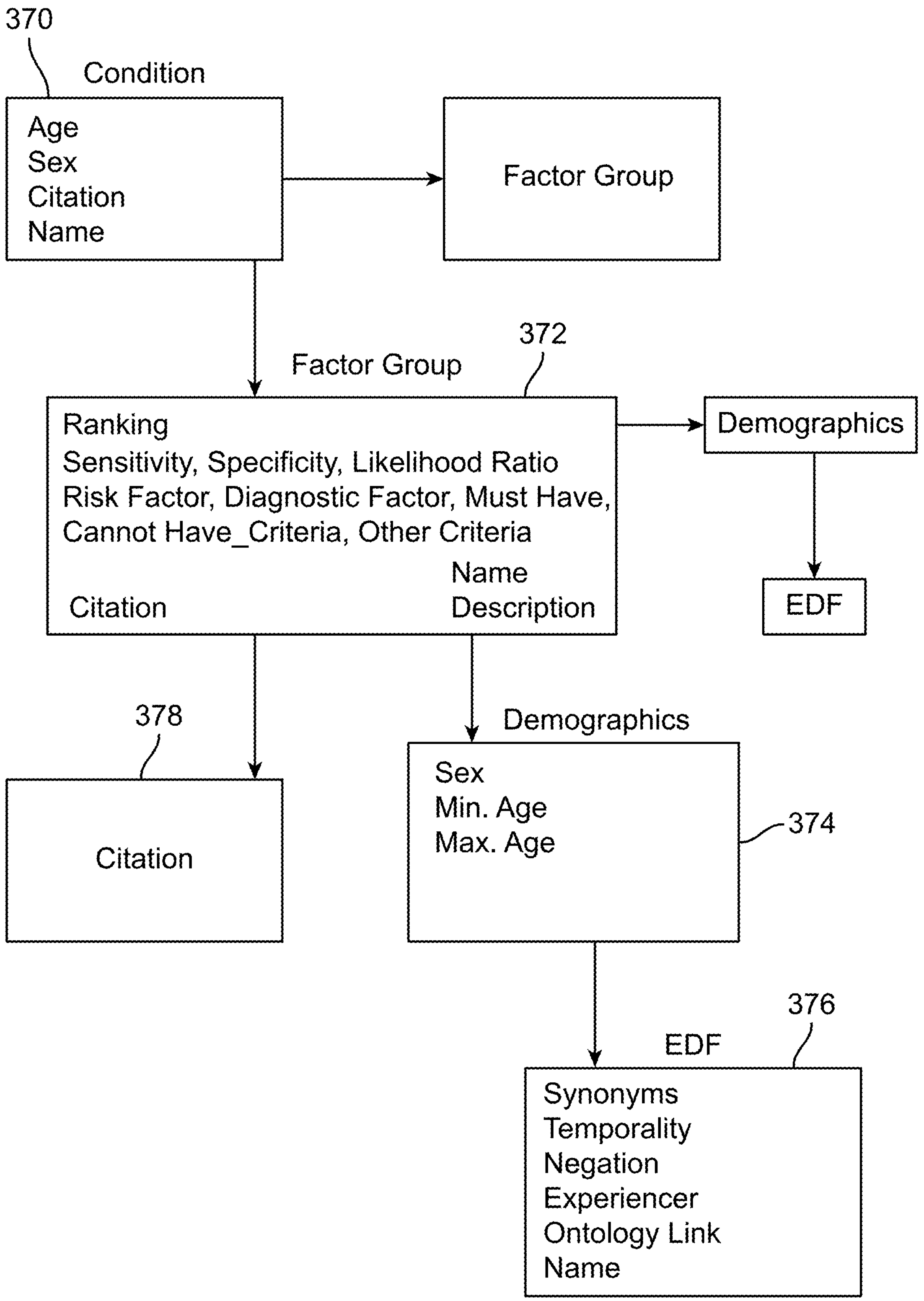
FIG. 4 provides more detail on the content of condition, factor group, demographics and EDF nodes.

FIG. 4 provides more detail on the content of condition, factor group, demographics and EDF nodes. As shown, condition node 370 may include properties for that particular condition such as a name, age (e.g., the condition can only occur in individuals having an age between 12 and 55), sex (e.g., the condition may only pertain to males or females), and a link to a citation describing that condition may also be present. Factor group 372 may include a ranking (applicable to each of the EDFs to which it is linked), a weight value (which may be used instead of the ranking) which may incorporate sensitivity, specificity and the likelihood ratio, a type which indicates whether the EDFs linked below the factor group are diagnostic factors or risk factors, and "must have" and "cannot have" criteria indicating whether or not the EDFs of this factor group must be present for the condition to occur or must not be present. Other criteria include a certain number of the linked EDFs must be present for the condition to occur (e.g., "at least two of the below diagnostic factors must be present"), or a points system may be used, each of the below factors receiving a number of points and a minimum must be reached before the condition is known to occur. Also included is a link to a citation 378 providing support in a medical evidence source for the use of the factors of the factor group in indicating the condition. Each factor group may also have a name (e.g., gastrointestinal symptoms) and a brief description taken from the evidence source.

The ranking of the factor group indicates how likely it is that the particular factors of the factor group have been caused by its linked condition (in the case of diagnostic factors), or how likely is it that the factors have caused the medical condition (in the case of risk factors). A ranking may be expressed in an evidence source using numerical values, or words and phrases that refer to the likelihood that a group of factors is caused by particular condition or have caused the condition, and may be directly extracted from the evidence source or may be added by person 81 reviewing that source.

Other condition dependent properties include sensitivity, specificity, likelihood ratio, incidence, and prevalence among other elements. These all may be combined with the ranking to provide a weight value for the factor group, the weighting being a function calculated outside of a factor group, although the weight value may be stored in the factor group if desired. A weight value may be calculated in a wide variety of manners, including using the ranking only; another technique is to use specificity and sensitivity to calculate the likelihood ratio (the probabilities of people with the factor having or not having the condition).

The condition-dependent properties within a factor group node may be added in a variety of manners. Some of the attributes may be automatically added when the factor groups are added to the knowledge graph based upon output from the NLP engine when it recognizes the input text. Or properties may be automatically determined by using external ontologies or taxonomies. Or person 81 may add properties to a particular factor group when reviewing the clinical concepts during extraction.

Demographics node 374 includes the demographics of EDF node 376 which must be true for that factor to indicate condition 370. By way of example, if the factor of EDF node 376 is only present in certain genders, or only below or above certain ages in the context of condition 370 (i.e., the factor can only indicate the condition if the patient meets the demographics), then that information is held in node 374. Holding these demographics related to a particular condition also ensures that the EDF remains independent and applicable to any of a number of conditions.

EDF node 376 may include only the basic information needed to represent a particular factor (e.g., fever, headache, nausea) such that node 376 is elemental and independent and may be used as a factor in other conditions. By only holding the basic information in node 376, and by holding properties for that factor that are only relevant to condition 370 in nodes 372 and 374 (or on edges between nodes 370 and 376), node 376 can be used as a factor for many conditions.

For all of the elemental nodes of a knowledge graph described herein (EDFs, EDIs, ETIs), such a node may be implemented using basic information such as a unique link (e.g., a code, unique identifier, URL, URI, etc.) to an entry in a suitable ontology which defines the concept (e.g., factor, laboratory test, examination, or therapeutic intervention) represented by the node. This entry is a unique, standardized code which acts as a single source of truth in a knowledge graph. Even though particular ontologies and taxonomies are used, any of the ontology links herein may link to a suitable ontology, taxonomy or hierarchy depending upon the concept. In addition to or instead of an ontology link, the node's unique name or other unique identifier (e.g., a UUID or universally unique identifier) may be used to uniquely define the concept.

Not only does an ontological link provide a unique definition of the concept, it also provides extra information, logic, and data about the concept that may not be present in the graph itself. For EDFs, the link allows us to reason and perform inferences in the SNOMED hierarchy. Similarly, for EDIs we can infer a result of one test as a result of another more generic test; for example, by knowing that White Blood Cell count of an individual is abnormal, we can infer that their CBC panel is abnormal as well—the ontology allows us to traverse and connect WBC count with CBC panel. For drug-based ETIs the ontology allows us to find "label" information for a drug which helps us compute a dosage for a patient, predict future adverse reactions, and obtain other information from the drug label. For example, using the ontology, an adverse reaction to penicillin helps us predict with some likelihood that an adverse reaction to carpabenems also exists given they both are β-lactams.

A node may also include its name (e.g., fever), synonyms (e.g., elevated temperature, pyrexia, febrile, feverish, etc., derived from the evidence source or from input by person 81), a description, temporality (T, a binary value indicating whether the factor was experienced in the past or now), negation (N, a binary value indicating whether the factor is present or not present), and experiencer (E, a binary value indicating whether the factor is experienced by the patient or family member). These values for TNE may be stored within node 376 or in a separate node linked to node 376, or not present. Further, given that there are three binary values, there may be as many as eight EDF nodes 376, each having a different value using the combination of these three values. Each of these eight EDF nodes is also independent and each may be used by many different conditions. For instance, an EDF node for fever may list temporality is now, fever is present, and experiencer is the patient. A second EDF node fever may list temporality is now, fever is not present, and experiencer is the patient. The other six nodes vary the other two attributes T or E.

An EDF, EDI or ETI is also made computational by virtue of its context in the knowledge graph. Its links to other nodes and conditions provide the ability to traverse between elements and conditions and allows reasoning capabilities. Further, logic for use in this reasoning is included within related nodes. For EDFs this logic is included within factor groups (e.g., a ranking) and demographic nodes (e.g., to whom the linked condition may apply); for EDIs the logic is within the investigation groups (e.g., a ranking) and result nodes (e.g., a result which indicates a condition); for ETIs the logic is within therapy groups (e.g., an indication ranking) and restriction nodes (e.g., when not used therapy). As mentioned before, this logic need not necessarily be held within particular nodes but may be held upon edges or in an associated location between the elemental concept and the condition.

Even though a factor group and a demographics node are shown between an EDF node and its indicated condition, it is optional to include these two nodes. If a particular diagnostic or risk factor is not dependent upon a patient's gender or age in order to indicate its linked condition, then a demographics node is not relevant and need not be present. Further, any properties of a factor group node such as ranking, risk factor or diagnostic factor, must-have, cannot have, etc. can be held on the edge that links a condition to its EDF, in which case an explicit factor group node is not needed. And diagnostic factors and risk factors may be held in different types of nodes, and the "must have" and "cannot have" criteria may also be represented by different types of EDFs. For a condition that does not have groups of factors that can be grouped conveniently, it may be simpler to link a condition directly to that factor without having any intermediate factor group node.

Figure 5:
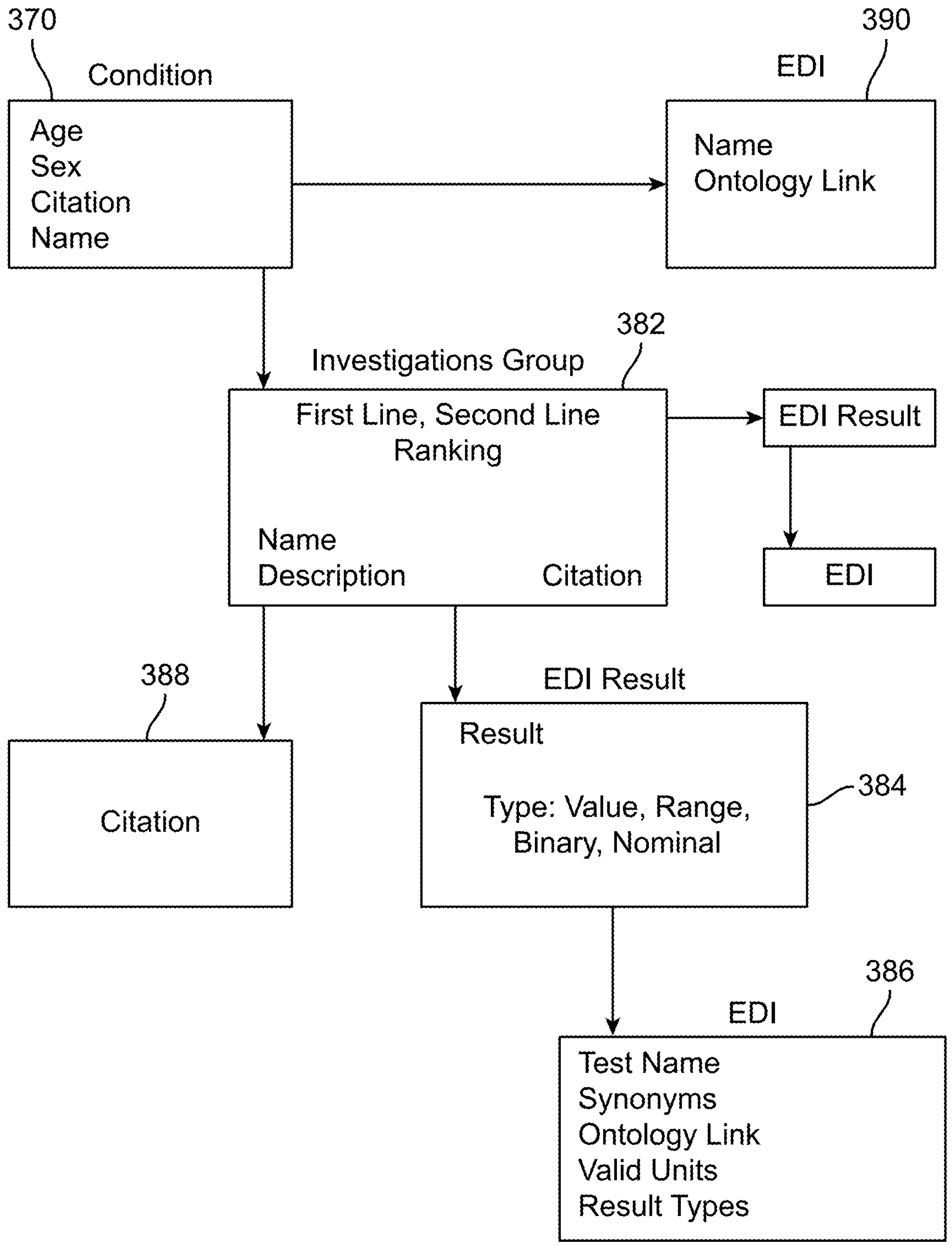
FIG. 5 provides more detail on the content of conditions, investigations group, EDI Result and EDI nodes.

FIG. 5 provides more detail on the content of investigations groups, EDI Result and EDI nodes. Investigations group 382 includes a name and description as above and a ranking (applicable to each of the EDIs to which it is linked) representing the likelihood that the linked condition is indicated when the result in the EDI result node is present. Also included is whether the group is first line, second line or emerging, etc., thus ordering the various investigation groups, which ordering may be adjusted by person 81. While an EDI node represents a laboratory test or examination that may be shared between many different conditions, its corresponding EDI Result node holds the particular result of that test which indicates that its linked condition is present. An EDI node may very well have two or more EDI Result nodes, each having a different result which links to a different condition.

Each EDI Result node 384 includes the actual result (e.g., "low," 32, greater than 100, in-between 50 and 100, yellowish, normal, etc.) from the laboratory test or examination that indicates the condition 370, units of the result, possibly reference range values, and the type of the result: a value, range, a binary, an ordinal, nominal, etc. Each EDI node 386 may include the test or examination name, synonyms, a link to one more taxonomies or ontologies (such as LOINC) using a unique code for that particular test or examination, and possible result types and valid units for that test or examination. Note that the types listed for a particular EDI Result 384 are likely a smaller subset than the result types listed in node 386. In another example, an EDI 390 may link directly to a condition and the condition-dependent properties and results may be stored in an associated location between condition 370 and EDI 390 such as on an edge. Thus, all condition-dependent properties indicating what is a valid result to indicate a linked condition are held outside of an EDI. Thus, each individual EDI node (whether for a laboratory test or examination) remains elemental and independent and may be used computationally to indicate various conditions. An EDI node may include only the basic information such as an ontology link, and optionally the other information.

Because the results of some laboratory tests and examinations can vary for the same test or examination (e.g., some machines have different reference range values, some are machine-readable and some are hand-readable, hospitals may use different tests for the same concept, different machines refer to the same test by a different name), it is advantageous to keep particular properties and their values within an EDI Result node rather than within the EDI node itself, thus ensuring that an EDI node remains independent and may be used for computation for any condition.

Even though an investigation group node and a result node are shown between an EDI and its indicated condition, it is optional to include these two nodes. Properties of an investigation group may be held on an edge or edges between a condition and an EDI. For a condition that does not have groups of investigations that can be grouped conveniently, it may be simpler to link a condition directly to that investigation without having any intermediate investigation group node. Even the actual result in a result node may be held on an edge, such as an edge between an investigation group and EDI, or between a condition and an EDI in the case where investigation group and result nodes are not present.

Figure 6:
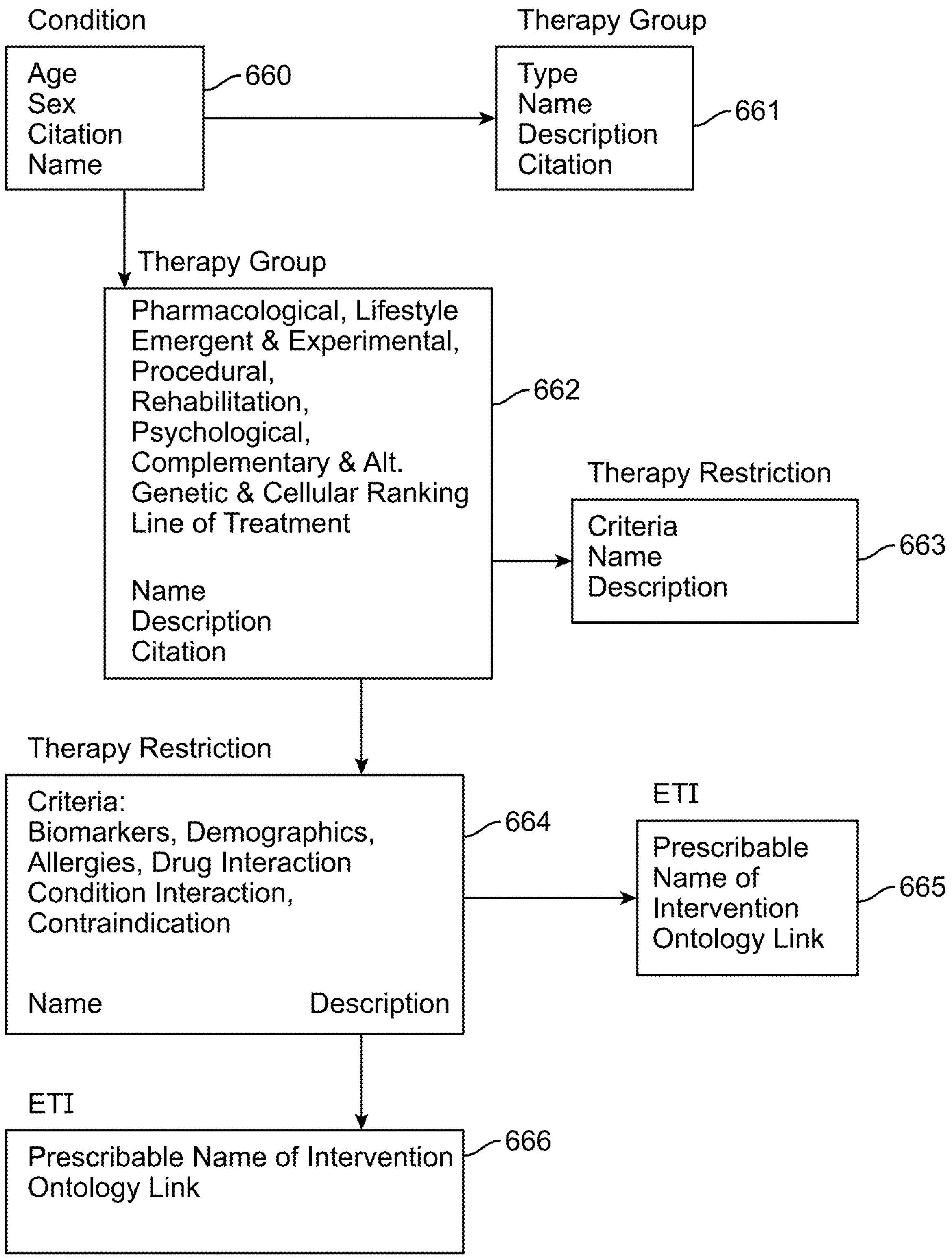
FIG. 6 is a block diagram showing details on therapy groups, therapy restrictions and elemental therapeutic interventions.

FIG. 6 is a block diagram describing in more detail therapeutic intervention and related nodes. As shown, any condition 660 of a knowledge graph may link to any number of therapy group nodes 661, 662. A therapy group is a high-level aggregation of similar therapies. For example, in the case of pharmacological (or drug-based) therapies, a therapy group may be constituted on the basis of the pharmacological properties of drugs (e.g. on the basis of mechanism of actions, such as beta blockers), on their chemical structure, or on their therapeutic effect (antibiotics versus anticoagulants). In the case of psychological therapies, a therapy group may represent an aggregation of psychological or behavioral therapies such as CBT, DBT, etc.

A therapy group node includes the properties of type, name, description and a citation link in a medical evidence source providing support for grouping particular therapies by type. The type property indicates the type of therapeutic intervention that is grouped below the therapy group node, i.e., any number of ETIs 663, 665, 666. The type of therapeutic interventions may be pharmacological or non-drug interventions such as lifestyle (e.g. preventative, nutrition, exercise, sleep), procedural (e.g., surgery, radiation, chemotherapy, cryotherapy), rehabilitation (e.g. speech therapies, occupational therapies, cardiac rehabilitation, neurological rehabilitation), psychological (e.g. cognitive behavioral therapy, dialectic behavioral therapy, group therapy, exposure, DBT, REBT), complementary & alternative (e.g. acupuncture, aromatherapy, ayurvedic therapy), genetic & cellular (e.g. gene therapy, stem cell therapy), or emergent & experimental (e.g. regenerative medicine, nanotechnology-based therapies).

A therapy group node holds condition-dependent properties including a ranking (e.g., a number mapping to usage probability of a drug for its linked condition). In general, the ranking indicates that the ETI is used X percent of the time as per the clinician's judgment to manage the linked medical condition. For example, penicillin G benzathine has a ranking of 1 for the condition syphilis, indicating that for 90%+ of syphilis cases, it is the drug that is prescribed. A ranking of 2 means that the ETI is used to treat the condition 30-90% of the time and if a 3 the ETI is used to treat the condition less than 30% of the time. Preferably, the ranking values for factor groups and investigation groups use similar numerals and scale, i.e., a 1 meaning highly indicative that the patient has the linked medical condition, while a 3 means less of a likelihood that the patient has a condition. The ranking scale used for all three groups may be inverted (i.e., 3, 2, 1 instead of 1, 2, 3), meaning that a highest final ranking value means the most likely condition. Also included is a line of treatment, i.e., whether the drugs in the group are first line, second line, etc.

Therapy group node 662 may be linked to any number of therapy restriction nodes 663, 664, and each therapy restriction node includes one or more criterion indicating why a therapeutic intervention (i.e., an ETI) linked to the therapy restriction node should not be used. These criteria can include: condition interactions (e.g., patients with cardiac issues should not be recommended certain exercises); patient biomarkers (e.g., patients with elevated creatinine should avoid high protein diets in certain conditions); patient demographics (e.g., elderly patients should not be recommended highly caloric deficit diets in certain situations); allergies (patients allergic to penicillin should not be given penicillin or amoxicillin); drug-drug interactions (patients on certain drugs should not be given other drugs that might lead to adverse reactions); a form contraindication (e.g., oral, intramuscular); other contraindications. Examples include "do not prescribe penicillin with another particular drug" and "do not administer to children under two years old."

Accordingly, a therapy restriction node may hold both condition-dependent properties and restrictions on use of its ETIs. In another example, consider the ETIs Excedrin Migraine and Excedrin Extra Strength: they both can be taken to cure migraine but it will be an off-label use of Excedrin Extra Strength while on-label use for Excedrin Migraine. Thus, although both these ETIs will have the same therapy group they will have separate restrictions regarding off-label versus on-label use. Each will have a separate therapy restriction node parent, with the property "FDA Approval" being "yes" for one and "no" for the other.

A therapy restriction node 664 may link to any number of ETIs 665, 666. An elemental therapeutic intervention (ETI) node may include the name of the actual prescribable drug or nondrug therapy intervention, its description, and an ontology link that connects the ETI to the intervention in an ontology (such as RxNorm in the case of drug-based therapies) where a formal description of the intervention is found. In the case of drug interventions, the actual prescribable drug includes at least the actual ingredient of the drug and the dosage. Other aspects of the prescription such as the form, route, frequency, and duration may be included as properties within the ETI, may be in the name or description of the ETI, or preferably are present in the ontology entry. In the case of nondrug interventions, the actual prescribable therapy (which may vary widely depending upon the therapy), e.g., specific name, duration, etc. may also be properties of the ETI, may be its name and description or preferably may be found via the ontology link.

The ontology link provides more information on the adverse effects of a drug and other nondrug properties for nondrug ETIs. In one embodiment, ETIs are based on branded drug names and not generic drugs. Hence, Tylenol and acetaminophen will use the same ETI for the same or similar dosage regimen. In another embodiment, ETIs may be based upon generic drug names, or may be based upon a mixture of both, for those drugs or therapies not having brand names.

Similarly, an ETI for a nondrug therapy also represents the actual prescribable therapy for the patient. By way of example, ETIs of the type psychological may specify exposure therapy, dialectical behavior therapy (DBT), rational emotive behavioral therapy (REBT) and others. In particular, ETIs may exist for three prescribable types of exposure therapy such as imaginal exposure therapy, in-vivo therapy and virtual reality exposure therapy, each possibly including frequency, duration and other specifics depending upon the type of therapy. A "prescribable" therapy represented in an ETI (whether a drug or nondrug therapy) thus represents a specific recommendation or prescription that a clinician gives to a patient for a particular therapy and its specifics will depend upon the particular therapy.

Even though a therapy group node and a restriction node are shown between an ETI and its linked condition, it is optional to include these two nodes. Properties of a therapy group may be held on an edge or edges between a condition and an ETI. For a condition that does not have groups of therapies that can be grouped conveniently, it may be simpler to link a condition directly to that intervention without having any intermediate therapy group node. If restrictions are not present for a particular therapy than no restriction node is needed. Further, any restrictions may be held on an edge, such as an edge between a therapy group and ETI, or between a condition and an ETI in the case where therapy group and restriction nodes are not present.

Figure 7:
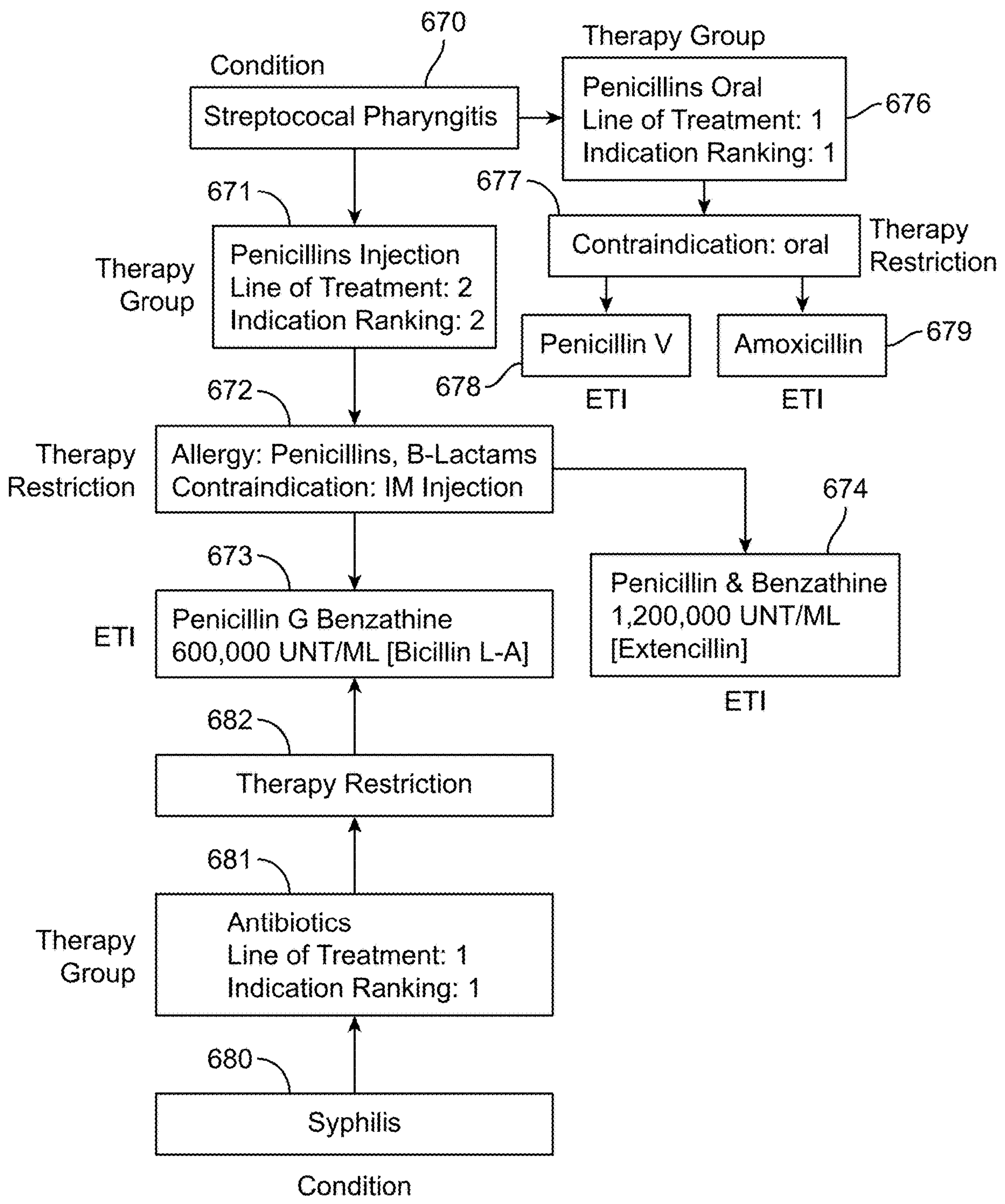
FIG. 7 is a block diagram of an example of elemental therapeutic interventions, therapy restrictions and therapy groups linked to medical conditions.

FIG. 7 is another example of a portion of a knowledge graph showing specifics for therapy groups, therapy restrictions and ETIs. As shown, therapy group 671 is for injectable penicillin and thus one of the restrictions in node 672 is a contraindication for intramuscular injections, along with two allergy checks for the drugs below the restriction node. It also includes the condition-dependent properties of line of treatment and indication ranking. ETI 673 is for a particular injectable penicillin ingredient showing the specific units per milliliter and the actual brand name within brackets. The other ETI 674 is for the same drug in a different dosage and having a different brand name within brackets. Note that two different ETIs are used because the dosage is different. Therapy group 676 is for oral penicillin and thus therapy restriction node 677 shows a contraindication for oral delivery; the allergy restrictions for penicillin and β-lactams are not shown. The two ETIs 678 and 679 are for drugs via oral delivery and the specific dosage and brand names are not shown. The therapy group 681 is for antibiotics that treat the condition syphilis 680; the group also has the properties line of treatment and indication ranking specific to the condition syphilis. It has a therapy restriction node 682 having restrictions (not shown) similar to those of node 672. Note that because ETI node 673 is elemental and contains no condition-dependent properties it can be used across conditions, such as conditions 670 and 680.

Other possibilities for a prescription for a condition include: "penicillin V 500 mg oral tablet," "penicillin V 3 mg/ml ophthalmic solution," "penicillin V 25 mg/ml oral solution." In other words, a clinician does not simply prescribe "penicillin V" for a patient; he or she prescribes "penicillin V 500 mg oral tablet," possibly along with other information such as frequency and duration. And if a drug in tablet form comes in two different dosages, e.g., 250 mg and 500 mg, each will have its own ETI. In general, drugs with different labels are represented by two different ETIs; they may link to the same therapy group though.

Preferably, the actual prescription information such as ingredients, brand name, dosage, form, route, duration, frequency, time of day is held in the entry of the ontology (RxNorm or FDB for drugs) to which the ontology link of an ETI links. Even more information such as class of drug (antibiotic, beta lactam, etc.) is available in the ontology. Similarly, for nondrug therapies, the ontology link contains the detailed prescription information. SNOMED may be used, or SNOMED codes may to some another tertiary ontology or database. This database may be an internal database designed via Web scraping, with the help of clinicians, etc. Therefore, the unique ontology link fetches information about the prescription.

Translation of Medical Evidence into Computational Elements

Medical evidence such as medical conditions, the diagnostic factors that indicate those conditions, the risk factors that may cause conditions, and the investigations (laboratory tests and examinations) that indicate conditions, may be extracted from a variety of sources and translated into computational elements as described in U.S. Pat. No. 11,869,674.

Similarly, treatments or therapies (i.e., therapeutic interventions, drug or nondrug) for conditions may also be extracted from a variety of sources (using the techniques described in U.S. Pat. No. 11,869,674 or by using other techniques) and translated into computational elements such as the therapy group nodes, therapy restriction nodes and elemental therapeutic intervention (ETI) nodes as described below.

Figure 8:
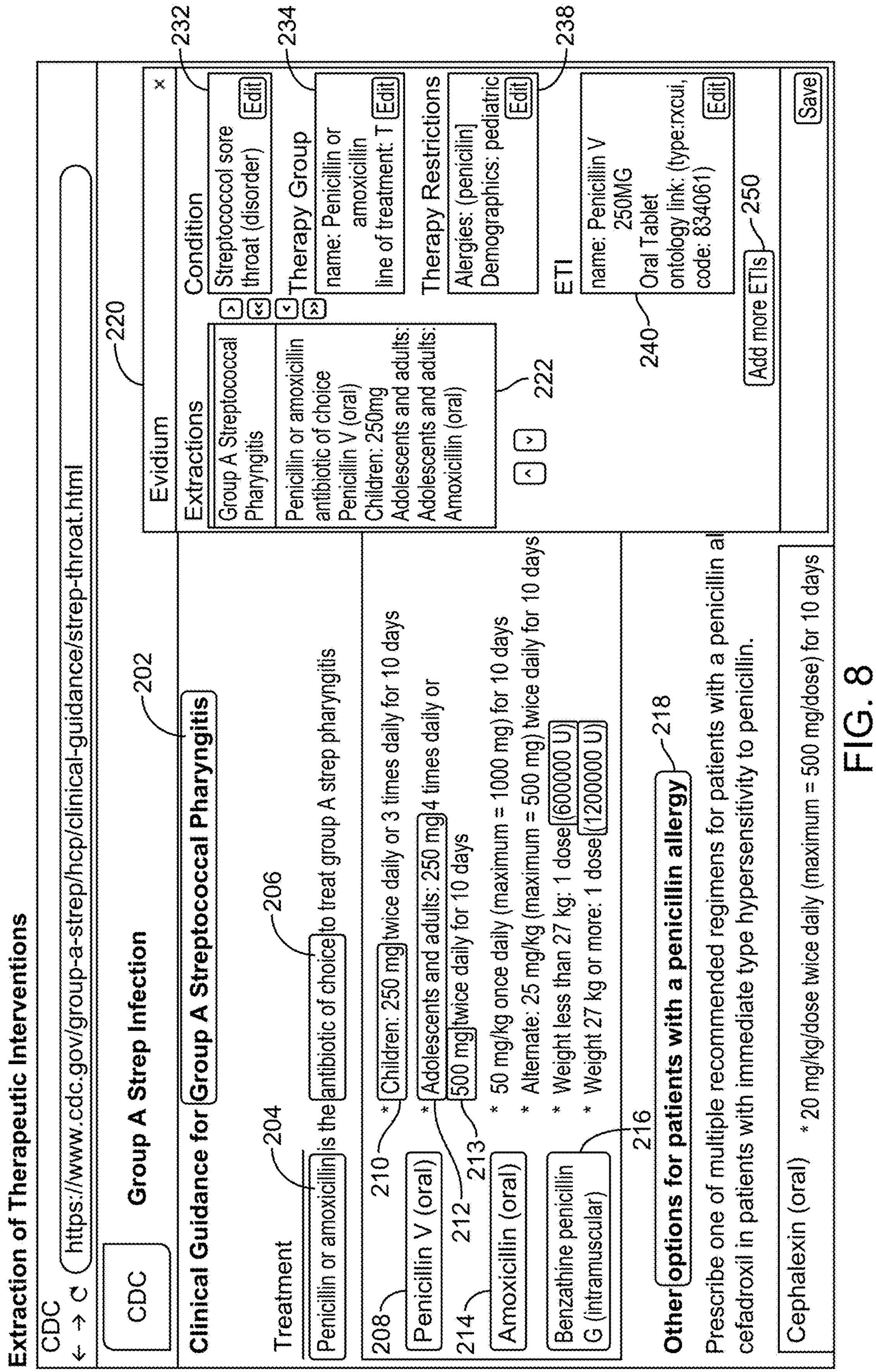
FIG. 8 shows an example of extracting therapeutic interventions from a medical evidence source.

FIG. 8 illustrates how therapeutic interventions (medical evidence) from an evidence source may be extracted and translated into these computational elements. As shown, any medical evidence source 200 (in this case a Web page) may be used from which to extract therapeutic interventions in this case, a drug therapy for a particular condition. In this example, natural language processing (NLP) has been used on the content of this page and it has identified, extracted and tagged (using a box for highlighting) numerous medical concepts. Tag 202 indicates the medical condition treated by the interventions below. Tag 204 indicates the drugs in general that may be used and tag 206 indicates they are the first choice. Tag 208 indicates a specific ingredient to be described along with a restriction and dosage 210 and dosage 212. Other specifics ingredients are tagged at 214 and 216. Tag 218 indicates an allergy warning for these drugs.

Overlaid over page 200 is a window 220 of a software tool used by a person to manually translate these extracted medical concepts into computational elements of a knowledge graph. Shown is a window 220 listing the extracted medical concepts from this page. Any of these extractions may be selected using a selection tool and transferred to boxes on the right-hand side of window 224 translating into these elements. For example, box 232 holds the name of the condition and may be edited, box 234 holds the name (from tag 204) of the therapy group and its line of treatment (inferred from tag 206), box 238 holds the therapy restrictions such as allergies (from tag 218) and a pediatric restriction (from tag 210). As shown, ETI 240 has been created for the specific prescribable drug tagged at 208 and 210, and an ontology link has been added for that specific drug. Selection 250 allows the user to add more ETIs, such as for penicillin V 500 mg (tagged at 213) or for amoxicillin 50 mg or 25 mg (tagged at 214). Currently, another ETI may be added for specific drug 216 which is intramuscular. In this fashion, therapeutic interventions are extracted from a medical evidence source and translated into computational elements.

Figure 9:
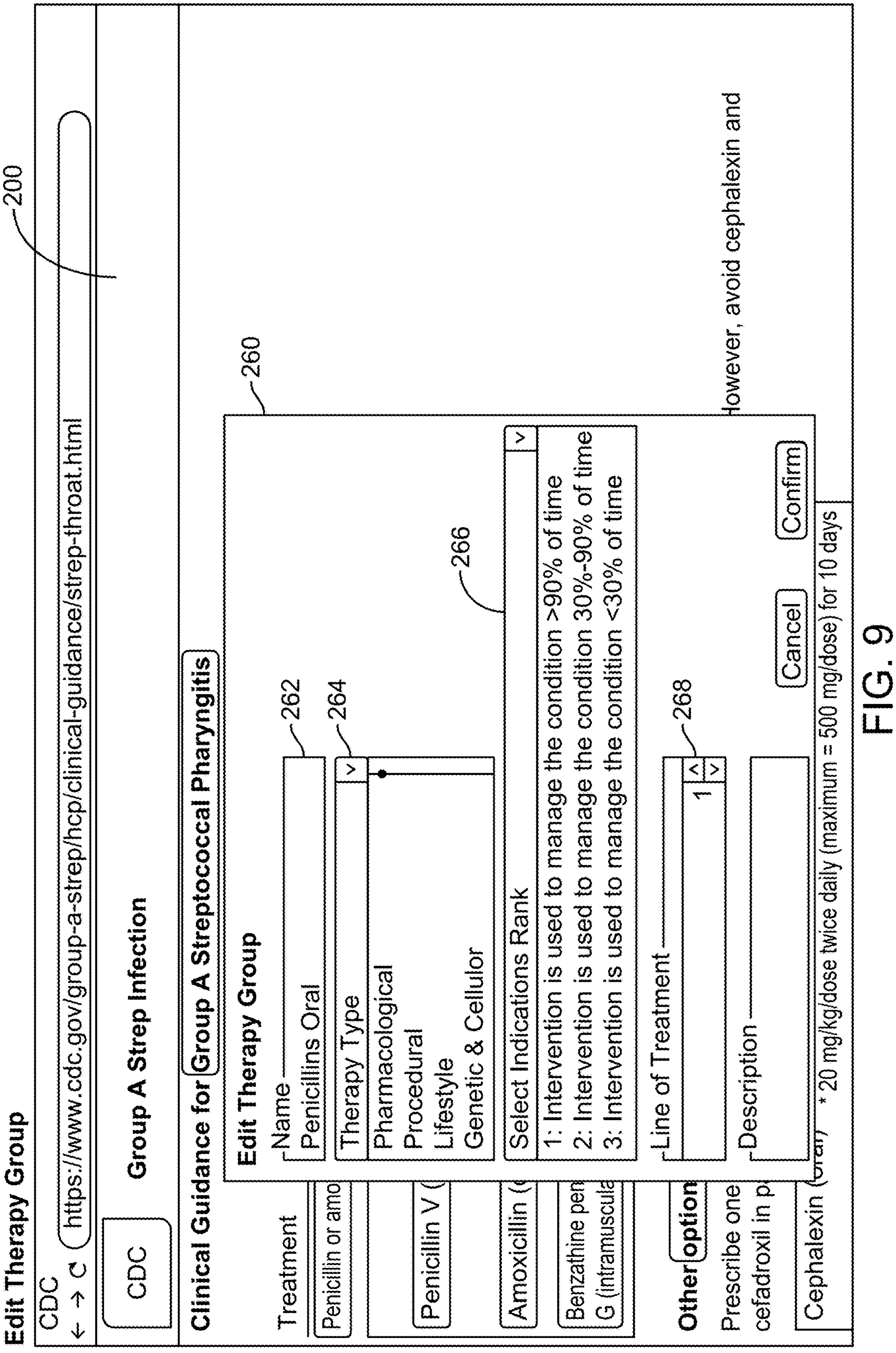
FIG. 9 shows editing computational therapeutic interventions.

FIG. 9 illustrates how a computational element created from a medical evidence source may be edited. Shown is a window 260 of the software tool used by a person to edit in this case a recently created therapy group node; medical condition nodes, therapy restriction nodes and ETI nodes may also be edited in this fashion. In this example, the user has decided that this therapy group shall represent only oral penicillins 262 and not penicillin 216. The therapy type 264 has chosen to be pharmacological and the ranking of this therapy group may be selected in menu 266. Menu 268 allows the line of treatment to be selected and a description may also be added. Although not shown, as the therapy group is limited to oral penicillins, an ETI for drug 214 may be added under this therapy group but not an ETI for drug 216. Another penicillins intramuscular therapy group may be created linked to condition 232 and this therapy group may include an ETI for drug 216.

Above are described embodiments using natural language processing (NLP) in order to extract medical concepts and translate them into computational elements. There are alternative embodiments that do not require use of NLP for this extraction. In a first alternative, a person reads through a medical evidence source (preferably in electronic form) and tags (or annotates, edits, etc.) the elemental concepts in that document (e.g., the medical conditions, elemental factors, demographics of factors, factor groups, laboratory tests, examinations, results from those investigations, investigation groups, therapeutic interventions, therapy restrictions, therapy groups, etc.) as well as indicating which elements are linked to other elements (e.g., which factors belong in a factor group and to which condition are they linked, which investigations belong in an investigation group and to which condition are they linked, which therapeutic interventions have which restrictions and to which therapy group and condition are they linked, etc.). Basically, the processing is handled by the person rather than the NLP.

In a second alternative, it is realized that many evidence sources (e.g., research papers, articles, etc.) have sections with keywords or tags similar to the elemental concepts of the knowledge graph (e.g., a keyword is "diabetes diagnostic factors"). Thus, instead of a person reading and manually tagging the entire document, a software application (or a person) extracts medical concepts by matching the keywords or tags of the document with the elemental concepts of a knowledge graph. In a third alternative, simple keyword extraction software (instead of LLM or ML) is used. The software extracts noun phrases from a medical evidence source, deletes noun phrases not related to medicine, the remainder being the medical concepts to be mapped to the knowledge graph.

Once the relevant medical concepts have been tagged, matched or extracted using any of these alternatives, the person using a suitable user interface may then organize or arrange these concepts into appropriate groups with appropriate linkages, may edit concepts, change names, disambiguate concepts, add an ontological link, and then add these concepts into the knowledge graph creating the appropriate linkages. The person may also add any of these elemental concepts to existing nodes in the knowledge graph (e.g., newly-found elemental factors are added to the knowledge graph and linked to a condition already existing, a new condition is added that is indicated by a particular result of an investigation already existing, a new therapy group of interventions with particular restrictions are created and added to an existing condition, etc.). Techniques for adding and linking any of these elemental concepts to a knowledge graph are shown and described in U.S. Pat. No. 11,869,674; other suitable techniques may also be used.

Use of Knowledge Graph

Figure 10:
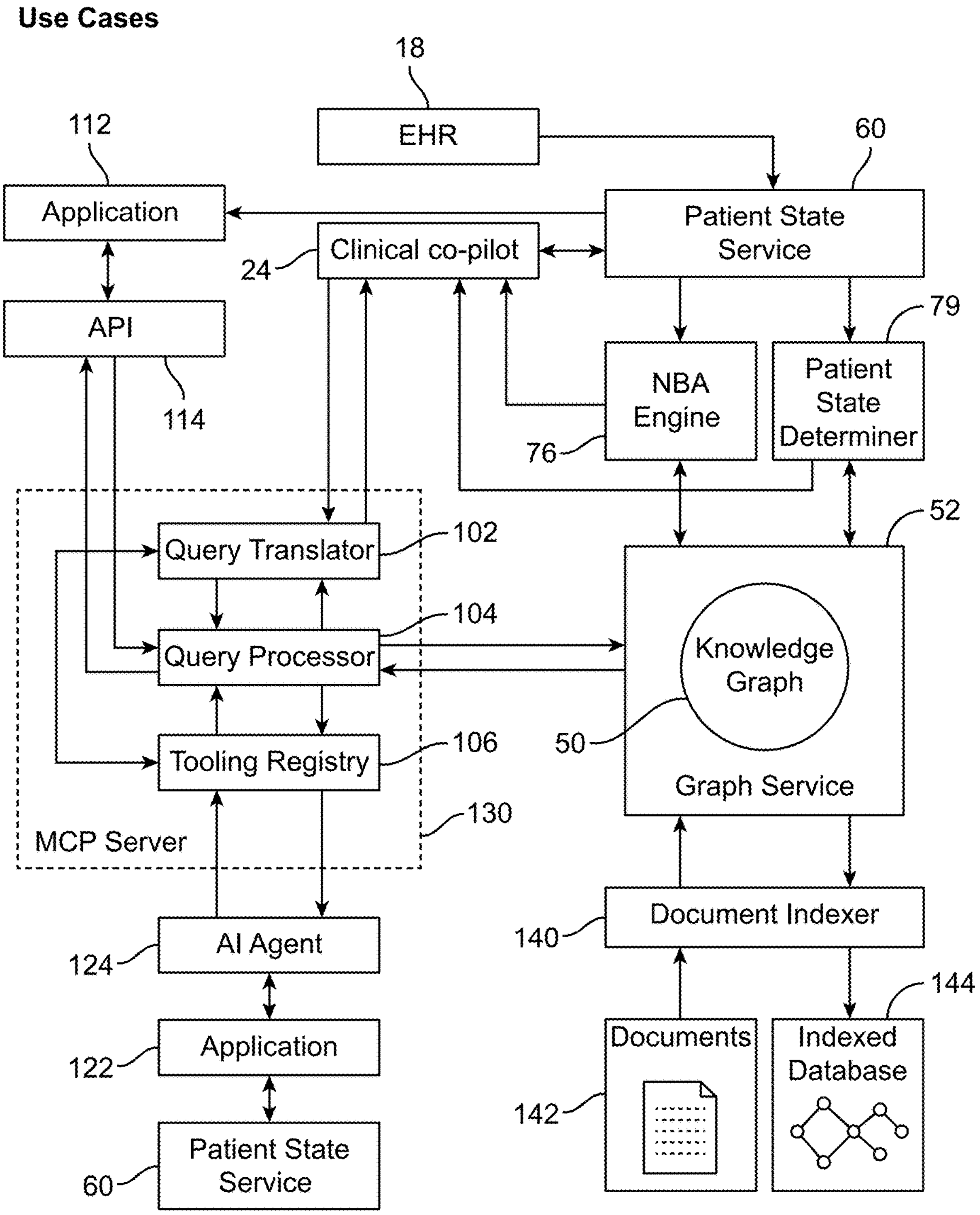
FIG. 10 is a block diagram showing possible use cases for the knowledge graph.

FIG. 10 is a block diagram showing various use cases applied to the knowledge graph. In the first three use cases the knowledge graph is queried using Co-pilot 24, application 112 or application 122; each of these use cases may be non-contextual or contextual, non-contextual meaning a query using only the knowledge graph itself (e.g. "give me all treatments for streptococcal pharyngitis") and contextual meaning the query includes patient data from patient state service 60 (e.g. "give me all drug therapies available for the condition that this patient most likely has"). Other examples are "what are all the medical conditions that the drug HCQ treats?" (non-contextual) and a query to determine if a particular patient should be given penicillin; the query compares drugs the patient is taking (from the EHR or patient state service) with restrictions corresponding to ETIs representing those drugs to determine if there is a penicillin allergy or not.

In a first use case, co-pilot 24 receives a natural language query from a user. In a second use case, a software application 112 presents a query via API 114. In a third use case, a software application 122 presents a query via AI agent 124. Depending upon the use case, query translator 102 converts a natural language query into graph query and is preferably implemented as an LLM. Query processor 104 executes a received graph query against knowledge graph 50 and receives a result back from knowledge graph 50. Tooling registry 106 includes a number of software tools which may be requested, including a tool to send a graph query to query processor 104. As shown, each of these three use cases calls each of these independent modules 102-106 directly.

Figure 11:
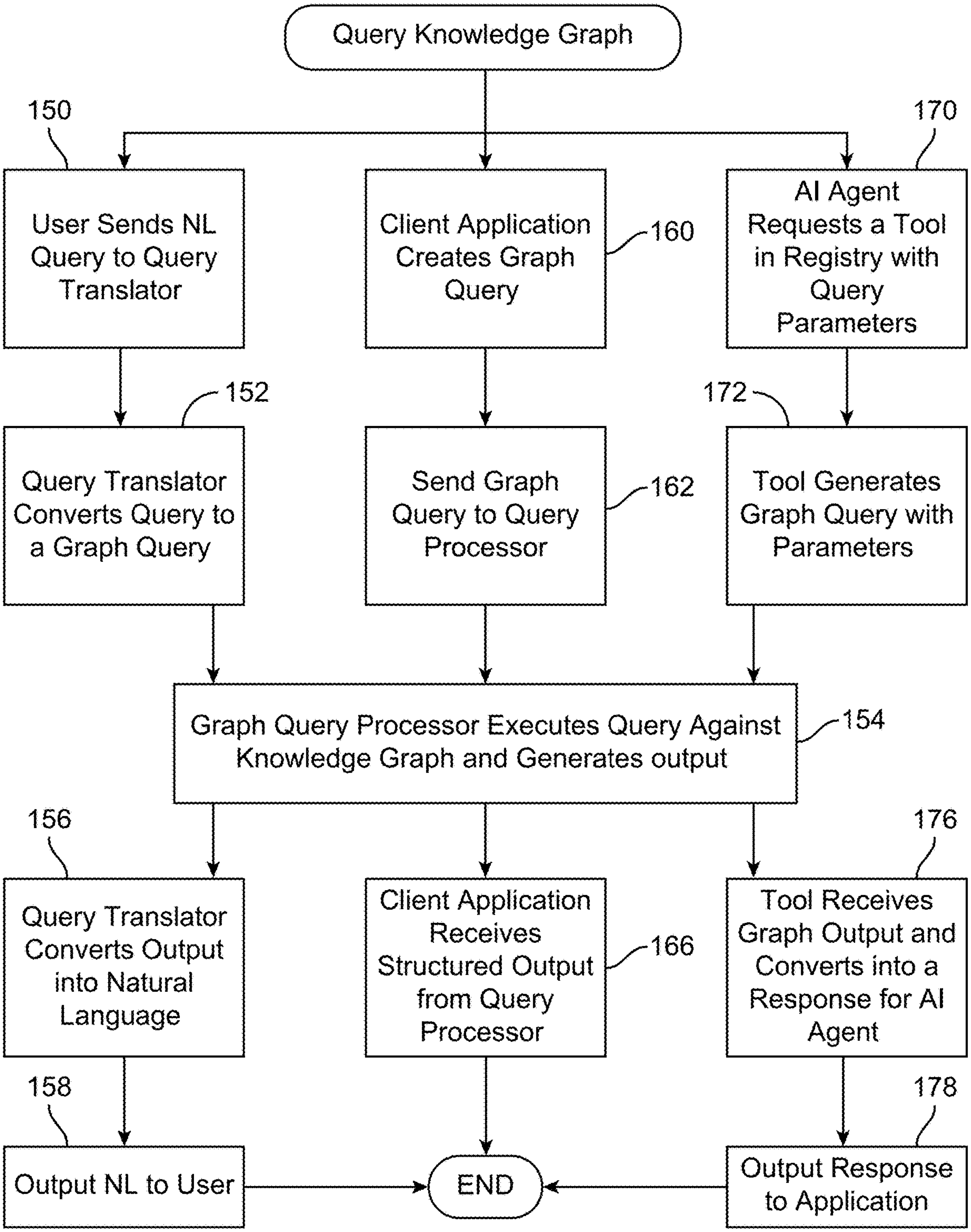
FIG. 11 is a flow diagram describing various use cases for querying the knowledge graph.

FIG. 11 is a flow diagram describing each of these three use cases. In a first use case in step 150, a user inputs a natural language query via copilot 24 (or via any suitable user interface) into query translator 102. The query may be about any aspect or contents of knowledge graph 50 including medical conditions, factors, investigations, therapeutic interventions, their related nodes, or the relationships or causality between them, and will be non-contextual if no specific patient information is included in the query. The query is contextual if it includes any patient specific information. Query translator 102 then converts this query into graph query, i.e., a query in the format expected by graph service 52 and knowledge graph 50. Next, in step 154 query processor 104 executes the graph query against the knowledge graph and generates a graph query output response from the knowledge graph. In step 156 the query translator then converts this graph query output back into natural language and then in step 158 this natural language output is output to the user via user interface 24. Interface 24 may retrieve patient data from patient state service 60 in order to formulate a contextual query.

In a second use case in step 160, client application 112 inputs a natural language query and creates a query (using JSON, XML or Protocol Buffers) of any aspect of the knowledge graph and uses API 114 to send a graph query in the format expected to query processor 104 in step 162. In step 154 the query processor executes the graph query against the knowledge graph and generates the graph query output response. In step 166 client application 112 receives the structured output (in J SON, etc.) via API 114 and creates a natural language response. Client application 112 may retrieve patient data from patient state service 60 in order to formulate a contextual query.

In a third use case in step 170, application 122 forms a natural language query of any aspect and sends query parameters (typically in J SON format with natural language query and context) to AI agent 124 (which includes tool calling capability) which then requests a software tool in tooling registry 106 using the query parameters (typically using JSON format specifying needed tool functionality). AI agent 124 may also accept a structured graph query depending upon the use case. In step 172 the requested software tool generates a graph query in the format expected and sends it to query processor 104. Next, in step 154 the query processor executes the graph query against the knowledge graph and generates the graph query output response. In step 176 the tool receives the graph query a response, converts into a response for the AI agent (typically in J SON with detailed output options). In step 178 the AI agent outputs a response to application 122 (typically JSON with processed treatment recommendations, natural language response, maintaining field name consistency with earlier responses). Application 122 may retrieve patient data from patient state service 60 in order to formulate a contextual query.

If application 122 helps clinical informatics teams in a health system to query a set of concepts abiding by certain logic, then most likely application 122 will forward a structured graph query to AI agent 124 which will then call the query processor from the tooling registry. If application 122 helps clinicians query in natural language then it will send a natural language question (and optionally context) to AI agent 124 which will call the query translator to convert the question into a graph query. Query translator 102 will send the response back to the AI agent via the tooling registry. The AI agent will then forward the graph query with context to the query processor (again via the tool registry). The query processor will execute the query on the knowledge graph and send it back to the AI agent via registry 106 and then the AI agent will send the structured response back to application 122. AI agent 124 is an AI dynamic pipeline which decides which tool to call in what order based on type of input in order to eventually execute the query.

In a variation on any of these three use cases, a modern context protocol (MCP) server 130 includes at least these modules 102-106 and each of co-pilot 24, API 114 and AI agent 124 interacts with MCP server 130 using a predefined syntax as is known in the art instead of accessing each module directly. Using the MCP server, co-pilot 24, API 114 and AI agent 124 each access (or "hit") an endpoint defined by the MCP server in order to reach the specific service they require (e.g., translator, processor, registry) and send requests and receive responses in a structured protocol. In other words, steps 150 and 158 access and use an MCP server endpoint instead of direct communication between translator 102 and interface 24; steps 162 and 166 also use an MCP server endpoint; and steps 170 and 176 also use an MCP server endpoint.

Other use cases include the following. Via an LLM query translator the steps include: user enters a natural language query "Find all medications of diabetes;" the query translator turns this query to the appropriate graph query; the graph query processor executes the query against the graph and retrieves results and sends them back to the translator; and the LLM translator then turns the results into natural language results and presents them to the user. Via an AI Agent, an agent may be an integrated component of any application pipeline. The application triggers an AI agent to select a tool from a tool registry and use it to send a query to graph query processor. Then, the graph query processor executes the query against the graph and returns the output to the tool registry. Via a direct API, an API request originating from an application contains a graph query. This query will be executed against the graph by the graph query processor and structured results will be sent back as a response.

The MCP server is a simple server with predefined syntax and protocols on how different actors (for example, LLMs, AI Agents, databases, etc.) are supposed to interact with one another. Hence, any of the use cases above can be carried out by the actor hitting the appropriate end point as is described in those points (for instance an AI agent hitting the tooling registry, the API hitting the graph query end point etc.).

As mentioned above, EDFs, EDIs and ETIs have characteristics that differentiate them from the prior art; each is atomic, may be placed in context, is composable, is computational, and may be used horizontally. In this flow we have: atomic (user query can be decomposed into knowledge elements in the graph); in context (to retrieve an answer for an input query, the graph query processor performs traversals within the graph as per the context of the query—which can also contain patient context as well); composable (user query as well as the answer are formed of composable knowledge concepts in the graph); computational (graph query processor can perform a number of computational traversals of the graph for executing a given query; it can also traverse through the graph using probabilities and ranking embedded in different context nodes as well); used horizontally (this is one of the different use cases described).

Knowledge Graph with Document Indexing

Figure 12:
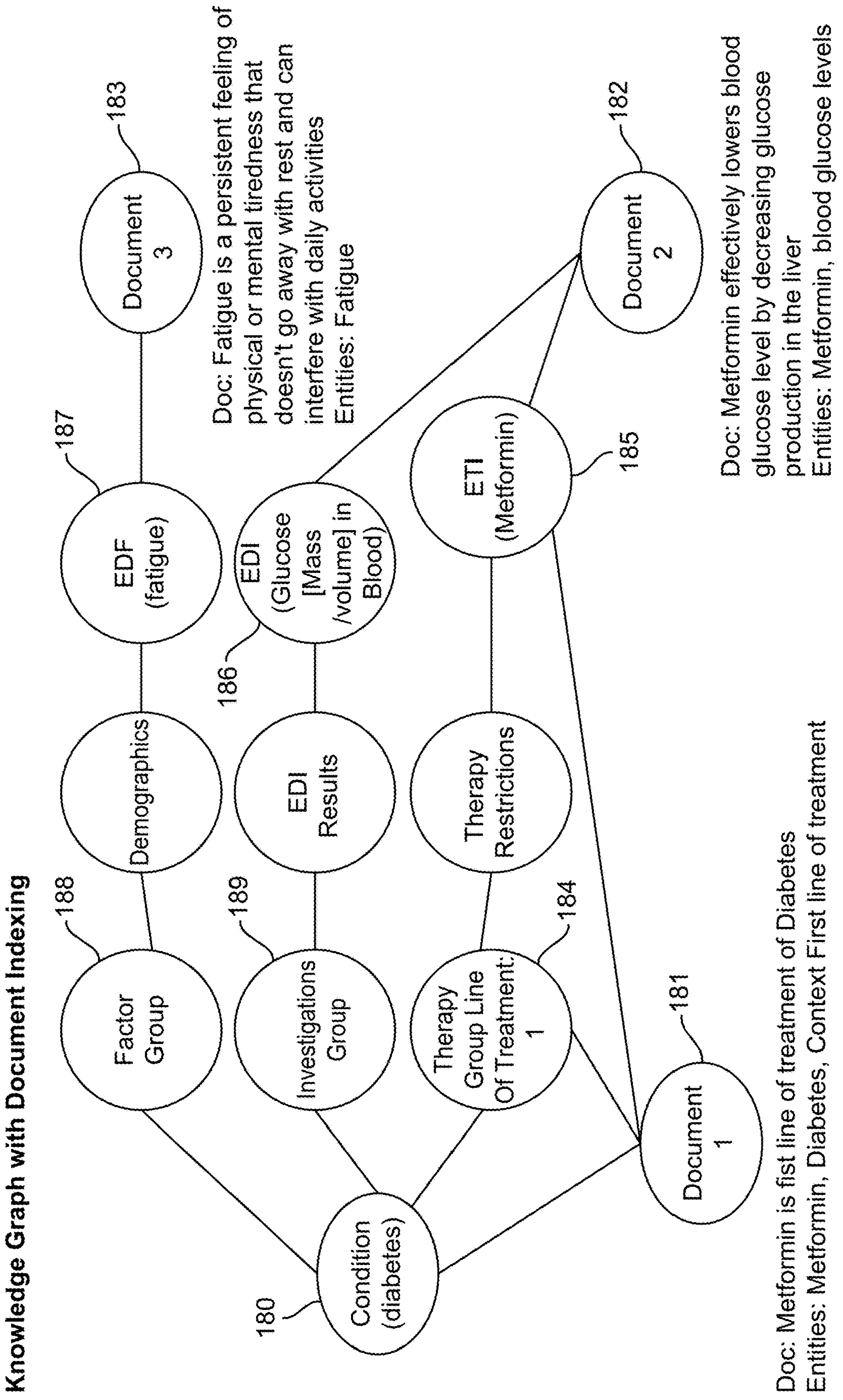
FIG. 12 illustrates a knowledge graph with document indexing.

FIG. 12 shows a knowledge graph with document indexing that may be created using a fourth use case of FIG. 10. As shown in FIG. 10, a document indexer software module 140 receives any number of documents 142 and creates an indexed database of those documents 144 such as shown in FIG. 11. Given a condition 180 such as diabetes, any number of documents 181-183 may be input into document indexer 140; these documents may relate to the condition in question but do not have to. The knowledge graph including condition 180 and its nodes 185-187 (and intermediate nodes) already exist; document nodes 181-183 and their links into the existing knowledge graph may be created as discussed immediately below.

Figure 13:
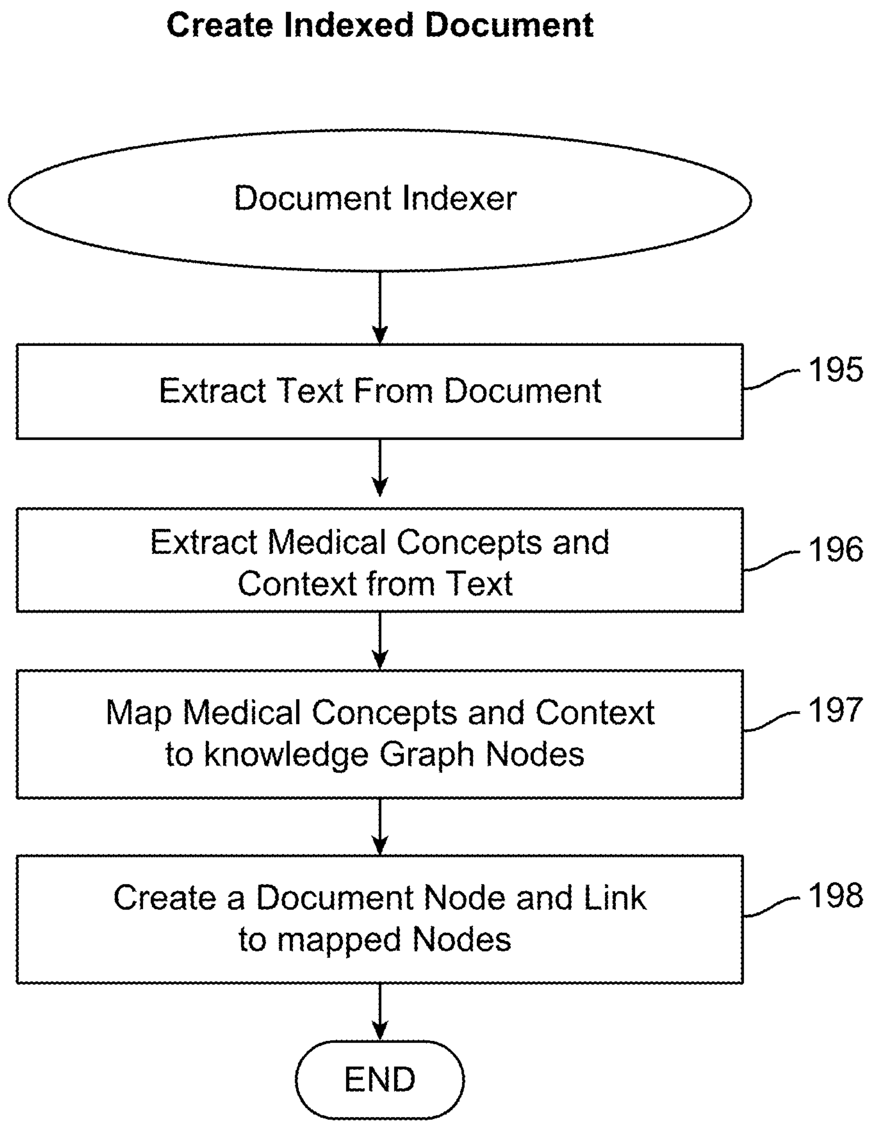
FIG. 13 is a flow diagram describing how to create an indexed document in a knowledge graph.

FIG. 13 is a flow diagram describing how medical concepts may be extracted from a document and then represented within a knowledge graph along with that document. Any number of documents may be input and each is processed as discussed below. The documents may all relate to a particular medical condition, a diagnostic factor or therapy, but need not relate to any particular medical concept. In a first step 195 the text is extracted from the document (e.g., a text file, PDF document, image, picture, Web page, etc.) using a suitable technology dependent upon the nature of the document, such as text retrieval, computer vision, optical character recognition, manual selection, etc. In step 196 the medical concepts and any related context is extracted from the text preferably using natural language processing (NLP) having models trained using medical terminology. In one embodiment, the techniques for text and medical concept extraction described in U.S. Pat. No. 11,869,674, such as by using a named entity recognition (NER) component of NLP, and/or the alternative techniques discussed above with reference to FIGS. 8 and 9 may be used.

Assuming that a first document includes the extracted text "metformin is a first line of treatment of diabetes," then the extracted medical concepts would be "metformin," "diabetes," and the context would be "first line of defense." Assuming that a second document includes the extracted text "metformin effectively lowers blood glucose levels by decreasing glucose production in the liver," then the extracted medical concepts would be "metformin" and "blood glucose levels." Assuming that a third document includes the extracted text "fatigue is a persistent feeling of physical or mental tiredness that does not go away with rest and can interfere with daily activities," then the extracted medical concept would be "fatigue." These extracted concepts and context may then be mapped as follows.

Accordingly, in step 197 the extracted medical concepts and context are then mapped to their corresponding nodes within the knowledge graph. For example, "diabetes" is mapped to condition 180, "metformin" is mapped to ETI 185, the context "first line of treatment" (for diabetes) is mapped to therapy group 184, "blood glucose levels" is mapped to EDI 186 (a laboratory test for blood glucose), and "fatigue" is mapped to EDF 187. This mapping may be performed in different manners such as by using a named entity linking (NEL) component of NLP as described in U.S. Pat. No. 11,869,674 or manually by a person.

Next, in step 198 a document node is created within the knowledge graph for the document being indexed and links are created from it to the mapped nodes of its medical concepts and context. The document node may contain any suitable identification of the document such as title, author, publication data, a unique identifier, a URL or other link to the actual document if online, etc. By way of example, a document node 181 is created for the first document and is linked to condition 180, therapy group 184 and ETI 185. In the other document examples, a document node 182 is created for the second document and is linked to ETI 185 and to EDI 186, and a documents node 183 is created for the third document is linked to EDFs 187. Although not shown, any document having medical concepts related to a line of treatment of an investigation may be linked to a node such as investigation groups 189, and a document having medical concepts related to any context in a factor group may be linked to a node such as factor group 188.

Once a knowledge graph has been enhanced by indexing any number of documents and creating their respective document nodes and links, any query related to documents may be formulated and submitted to the knowledge graph using any of the techniques described in FIGS. 10 and 11 above. By way of example, if a query is for "all documents containing a first line treatment for diabetes," we traverse from condition 180 down to a therapy group 184 which includes "first line of treatment" and from there can traverse to the document represented by document node 181. If the query is also for the actual treatments, we can traverse down from node 184 or possibly from node 181 to any matched treatments such as node 185. Other possible queries are for "documents with first-line laboratory tests," documents describing highly-ranked factors for particular conditions, documents describing particular therapies, documents describing particular diagnostic or risk factors, etc. Unlike semantic search can be very unreliable in performing a word search in a document, this document indexing technique can be very reliable.

In a simple example, assume a document contains "Metformin is the first line of treatment for type two diabetes." The document is broken down and mapped to concepts in the graph: "first-line-of-treatment" maps to→TherapyGroup associated with Metformin ETIs suggesting Line Of Treatment=1; "Metformin" maps to→multiple prescribable Metformin ETIs; and "type 2 diabetes" maps to→EDF containing the following SNOMED concept "44054006|Diabetes mellitus type 2 (disorder)|". A document node is then created with a unique identifier and this node is linked to the three nodes created.

As mentioned above, EDFs, EDIs and ETIs have characteristics that differentiate them from the prior art; each is atomic, may be placed in context, is composable, is computational, and may be used horizontally. In this flow we have: atomic (entities are mapped to elemental concepts—ETIs/EDIs/EDFs—in the graph along with the context associated with these elemental concepts and associated conditions); in context (the mapping occurs such that the context of an elemental concept is linked as per the context of the document); composable (at the end, the document is represented as a composition of the difference concept nodes it has been linked with); computational (the querying of a document involves computational traversal in the knowledge graph); used horizontally (one of the different use cases described).

Determine Patient State

Patient State Determiner 79 and NBA engine 76 may utilize information of ETIs in a knowledge graph coupled with information in a patient EHR to make improved inferences and improve reasoning. Such inferencing is particularly useful when analyzing claims data (where typically there is less information on factors and investigations): a drug the patient is taking (from the EHR or patient state service) may be used to infer medical conditions, factors or investigations using the ETI of that drug.

Figure 14:
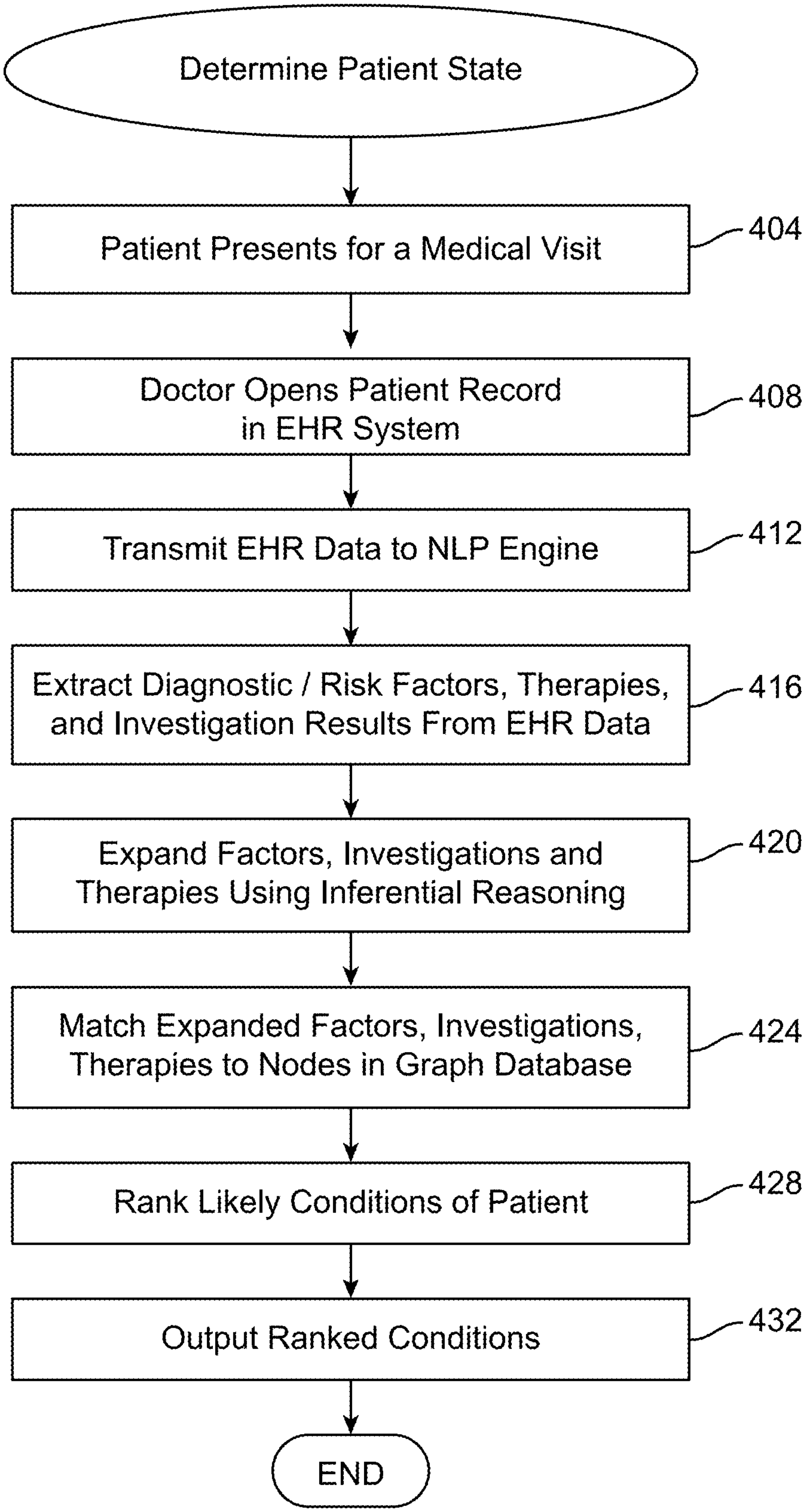
FIG. 14 is a flow diagram for determining a patient state.

FIG. 14 is a flow diagram describing how the patient's state including most likely condition or conditions may be determined. The platform may first load the entire knowledge graph into its memory or is enabled to send queries to the knowledge graph which may be located remotely. In a first step 404 a patient presents for a medical visit with a clinician, e.g., an in-person visit or by telephone, computer, or any other suitable telemedicine scenario. Alternatively, the patient has presented in the past and the clinician is reviewing the patient's chart without the patient being present. Or, the flow is being executed upon the patient's EHR without any patient available and any needed answers are supplied automatically, using default answers, or by a best guess by a clinician.

In a next step 408 the clinician uses EHR system user interface 20 (or other suitable user interface such as application 24) to open the patient's electronic chart in the EHR system. The EHR system detects the clinician's context, the patient context (e.g., a medical record number) and sends this information to the backend systems of platform 10. The clinician may also decide to enter patient data into the EHR via clinical co-pilot 24 from which the patient data is fetched using EHR APIs.

In step 412 platform 10 downloads the patient's medical history from his or her chart via the clinical co-pilot 24 (which may be integrated with the EHR system) and transmits the textual information to the NLP engine 74 via patient state service 60. Included within this medical history are family history, patient history, narrative clinical documents such as diagnostic reports, discharge notes, any clinical notes that a clinician had entered previously or has just entered, including simple notes, SOAP notes, structured column notes, consultant notes, etc. Further, any transcriptions may be included as well as transcriptions transcribed from a microphone using speech recognition software.

Next, in step 416 patient state service 60 calls NLP engine 74 in order to extract the diagnostic factors, risk factors, investigation results (including laboratory test results and examination results) and current drug and nondrug therapies that the patient is undergoing from the patient's medical history. Preferably, the NLP engine is initialized with the EDF, EDI and ETI nodes from the knowledge graph in order to facilitate finding those same concepts within the patient medical history. NLP engine 74 may also use embedding service 76 in order to extract the relevant factors, investigations and therapies from the patient's medical history, resulting in factors, investigations and therapies that are either known to be present or known to be absent in the patient's state and that are the same or similar to EDFs, EDIs and ETIs in the knowledge graph.

This extraction is automatically performed by the platform 10. Basically, the NLP engine looks for clinical concepts in the medical history that may match nodes in the existing knowledge graph. Further, the NLP engine uses the full context of the patient chart and can disambiguate concepts; it can distinguish between "patient examination," "pulmonary embolism," and "peripheral edema," which may all have the acronym PE in the patient chart. The NLP engine may also use the ontology link in each EDF, EDI or ETI in order to disambiguate concepts: given a concept from a chart, an ontology link from an EDF, EDI or ETI may be used by the NLP engine to traverse up (or down) a hierarchy of concepts in order to explore and find a concept already in the graph in order to match the chart to the graph. This traversing is useful when two concepts in the chart have the same name but different meanings. By way of example, the phrases "cold" or "feeling cold" or "feeling a little cold" can be ambiguous about whether the patient is describing a condition or a symptom. The platform uses the ontology link in an EDF to understand whether "cold" is a finding (i.e., a factor) or is a condition in the context of the patient's chart, thus distinguishing between these phrases. All of these techniques provide greater accuracy for the platform.

In step 420 reasoning service 72 uses inferential reasoning in order to expand the factors, investigations and therapies that were extracted from the EHR data in step 416 and may use an internal or external ontology or any other suitable medical taxonomy or hierarchy in order to perform this inferential reasoning. By way of example, if one diagnostic factor is "double quotidian fever" the service finds the parent of that which is "fever," infers that another diagnostic factor of the patient is "fever" and traverses upward in the ontology adding all other relevant diagnostic factors that are parents of "fever." If a negation is present, e.g., a diagnostic factor is "no fever," then the service traverses down in the ontology to infer that the patient does not have "chronic fever" nor "intermittent fever," and other possible children. In another example of expanding therapies (drug or nondrug), if the patient is taking amoxicillin the service infers that the patient is taking an antifungal medication by traversing up the ontology. Investigations may also be expanded. For instance, if the patient did a white blood cell test with a particular result it may be inferred that this test was part of a CBC blood culture having a corresponding broader result and thus a CBC blood culture investigation is now a known investigation of the patient's medical history.

In step 424 all of these extracted factors, investigations and therapies as well as all expanded factors, investigations and therapies inferred to be present in the patient are matched to corresponding nodes in the knowledge graph, for example by matching to EDF, EDI and ETI names or synonyms, thus matching to the most specific level of a medical concept. Or, medical codes found in the patient chart for these factors, investigations and therapies may be matched to corresponding codes in an EDF, EDI or ETI or in its ontology link. For instance, the patient diagnostic factor of "high fever" from the patient's medical history may be matched to the EDF "high fever." Both factors may also be represented in the same format or data structure thus allowing comparison and a determination that the patient's diagnostic factor matches the EDF in the knowledge graph.

When we match a patient diagnostic factor of "fever" to the graph database we are matching the patient's factor to the EDF fever node 310 not to its demographics node 306 or 352. The reason is that it is unknown at this time what the patient's condition or conditions might be and by matching only to the EDF fever node it leaves open the option of concluding that any of various conditions linked to fever might be possible. Attempting to match not only to fever node 310 as well as to demographics node 306 might preclude a match if the demographics do not match. By allowing a match irrespective of any of the demographics nodes we can later conclude during ranking any potential conditions linked to the fever node, assuming that the demographics match. Similar matching occurs with respect to EDI nodes; we match extracted patient laboratory tests and examinations to EDI nodes (e.g. 328-332) irrespective of their EDI result nodes (e.g., 322-326). Similarly, therapies are matched to ETI nodes without taking into account any demographics of the linked therapy restriction node.

Thus, the demographics nodes corresponding to matched EDF nodes are taken into account during ranking when reasoning occurs to determine if the patient has the particular condition related to that EDF node. For example, if the patient's factor matches EDF fever node 310, but demographics node 306 indicates that it is only found in women, then condition 300 would not be ranked or concluded for a male patient. Similarly, if demographics node 352 indicates that its associated fever is common in men over 50 years old and the patient is a male over 50, then it is certainly possible that the patient will be diagnosed with condition 340. In a similar manner, an EDI result node is used to determine if a matched EDI node is relevant for its associated condition (i.e., data in the patient chart matches the EDI result) when performing step 428. Further, for ETIs, demographics in a therapy restriction node are used to determine if its linked condition is relevant in step 428 (i.e., data in the patient chart matches the demographics). For example, assuming a patient chart with: "Pt. is a 10 yo m, wt 24 kg with no known pen allergy. Amoxicillin prescribed for BID administration." We know that a 10-year-old male took amoxicillin 500 MG BID. We do not know the condition but the ETI can be matched straightforwardly using a semantic matcher or as described immediately below. Now it is possible that this ETI connects with five different conditions but only to two conditions with demographics of age "pediatric," in which case the likelihood of those two conditions will be increased during ranking and the other three conditions will have a greatly decreased likelihood because the demographics do not match that of the patient.

In an example of matching to an ETI node, consider a patient chart with: "Pt. is a 10 yo m, wt 24 kg with no known pen allergy. Amoxicillin prescribed for BID administration." In step 416 the NLP engine performs concept extraction to obtain the concepts: "10 yo", "wt 24 kg", "no known pen allergy", "amoxicillin", "BID." In step 424 (assuming no expansion done) entity linking matches these concepts to the closest possible concepts in the knowledge graph (if possible); the NLP engine uses semantic matching models (e.g. Embedding service 77) as well as Reasoning engine 72. For example, the amoxicillin concept may be mapped to the ETI Amoxicillin (name: Amoxicillin 500 MG Oral Tablet ontology_link: {type: rxcui, code: 308192}) in two steps. In a first step we find the top N semantically similar graph nodes for this extracted concept. For example, for "amoxicillin" we find ETIs like "Amoxicillin 100 MG Oral Tablet" and "Amoxicillin 250 MG Oral Tablet." In a second step, we can choose the top-scored graph node from above if we do not have enough context, but since we have more context, we can further fine tune the scores using the reasoning engine. The reasoning uses the demographics contained in a therapy restriction node to match to the ETI node having demographics most closely matching the patient chart of a 10-year old male. Hence, ETI node Amoxicillin 500 MG will be the top most ETI which is matched to the concept amoxicillin if it has demographics of "pediatric" in its therapy restriction node.

In one embodiment, partial matching is performed during step 420. By way of example, as extracted factors, investigations and therapies are each in turn considered for expansion using inferential reasoning, the platform will match each to a corresponding node in the knowledge graph in order to find the link to an appropriate ontology for expansion. As expansion occurs (by traversing up or down the ontology) the platform can match inferred patient diagnostic factors to the corresponding node in the knowledge graph, e.g., inferring that the patient has "fever" from a patient factor of "double quotidian fever" means that the platform can also match the "fever" node in the knowledge graph. Matching may occur in other manners, such as by matching all expanded factors, investigations and therapies in step 424 rather than during the expansion of step 420.

In step 428 the platform computes rankings of the likely conditions of the patient in order to present a differential diagnosis. As mentioned above, each factor group and linked investigation group includes a ranking value indicating how likely it is that its particular factors or investigations will manifest given its condition. Each therapy group includes an indication ranking value indicating how likely it is that the patient has its linked condition if one of its linked ETIs is present in the patient. For example, an ETI representing PAXLOVID (a treatment for COVID-19) will have an indication ranking value strongly suggesting that the patient may have the condition COVID-19.

Step 428 looks at the factor group nodes, investigation group nodes and therapy group nodes for each matched EDF node, EDI node and EDI node to determine a final ranking value of their associated conditions. The knowledge graph may be traversed in any manner to collect the ranking values from these group nodes and combine them to produce the final ranking value for a condition. By way of example, if ETI node 303 is matched the ranking value in node 301 will be used in combination, if EDI node 328 is matched the ranking value in node 316 will be used in combination, but if EDF node 310 is not matched then the ranking value in node 304 will not be used (unless EDF node 312 is matched). In one embodiment, step 428 starts with each matched EDF, EDI or ETI node, traverses upward taking into account demographics, EDI result and therapy restriction nodes, collecting ranking values from the factor group, investigation group and therapy group nodes, and combining these ranking values to produce a final ranking value for the linked condition, a higher final ranking value meaning it is more likely that the patient has the condition. Thus, the sum of these ranking values associated with all matched nodes is the final ranking value of the linked condition.

As mentioned above, even though an EDF, EDI or ETI node is matched, it will carry no weight and the associated ranking value in its parent factor, investigation or therapy group node will not be used if the patient does not meet the demographics in a demographics node between the EDF node and the condition, does not meet the specific result in an EDI result node in between the EDI node and the condition or does not meet the demographics in a therapy restriction node between the ETI node and the condition. (A ranking value in a group node will be used if a different EDF, EDI or ETI does match the patient chart, e.g., if EDF fever 310 is not present but EDF nausea 312 is, then the ranking value in factor group node 304 will be used.) Further, a matched EDF node rule in or out a condition if the condition-specific criteria in the factor group corresponding to that EDF node are not satisfied. For instance, if a factor group lists certain "must-have" diagnostic factors then the associated condition will not be considered if those diagnostic factors are not present; similarly, if certain "cannot have" diagnostic factors are listed then the associated condition will not be considered if those diagnostic factors are present in the patient.

Optionally, each EDF, EDI or ETI node may include a noise value representing how much relevant information content the node has relative to other nodes. For example, fever node 310 provides a certain amount of information whereas double quotidian fever node 356 is more specific and provides even more information, thus having a greater noise value. This noise value may be stored separately in a group, incorporated within the ranking value of a group, or stored within the EDF, EDI or ETI itself. In an alternative embodiment, instead of simply combining ranking values of groups, a parameterized weighting function may be used to combine a ranking value of a group with any of the noise values of its EDFs, EDIs or ETIs, the sensitivity, specificity, or likelihood ratio properties in order to compute a weight value for each factor group, investigation group or therapy group. These weighted values for each group may then be combined to compute a final weight value for a particular condition in order to rank that condition against the other conditions, a higher final weight value meaning that it is more likely that the patient has that condition. Other techniques for assessing the relative importance of factor, investigation and therapy groups may also be used; the weighting function may weight these groups differently from one another. Or, we compute a two- or three-dimensional sensitivity, specificity and likelihood ratio for each group and then compute a final weight value for each condition based upon those ratios.

In any case, the sum of the ranking values (or weight values) for all matched EDFs, EDIs and ETIs for a given condition informs the final ranking value (or final weight value) for a particular condition. The top N conditions may be considered the differential diagnosis for that patient, N being a design choice and being a suitable number for consideration, further calculation or display, such as 1, 3, 5, 10, etc.

In step 432 these top N conditions are output for display upon clinical copilot 24 for viewing by the clinician, may be output in any suitable data structure for further processing by another software application, may be used as input to determine a next-best action as described immediately below, or may be output for any other purpose. These output conditions may simply be listed in order of their ranking without further information, may each be listed along with a ranking value, may each be listed along with a probability value of being present, etc.

In a simple example, assume a patient chart with: "Patient has sore throat and is taking penicillin V." Both penicillin V and sore throat may be linked to multiple conditions. But when a ranked list of conditions to which these concepts link is generated, Strep Pharyngitis comes as the top-most diagnosed condition.

As mentioned above, EDFs, EDIs and ETIs have characteristics that differentiate them from the prior art; each is atomic, may be placed in context, is composable, is computational, and may be used horizontally. In this flow we have: atomic (in step 424 patient data is matched to the most specific level of medical concepts); in context (at node 420 expansion takes place based on a patient's context, for instance if a patient has a contraindication against oral drugs, they will be administered an injectable drug and hence only injectable drugs will be expanded by this reasoning); composable (the extracted and expanded concepts at steps 416 and 420 compositionally represent the patient state; further, conditions are predicted to add another concept to this compositional state); computational (the expansion and ranking steps 420 and 428 are accomplished by executing logic present in the different nodes described); used horizontally (this is one of the different use cases described).

Determine Next-Best Actions Per Condition

Figure 15:
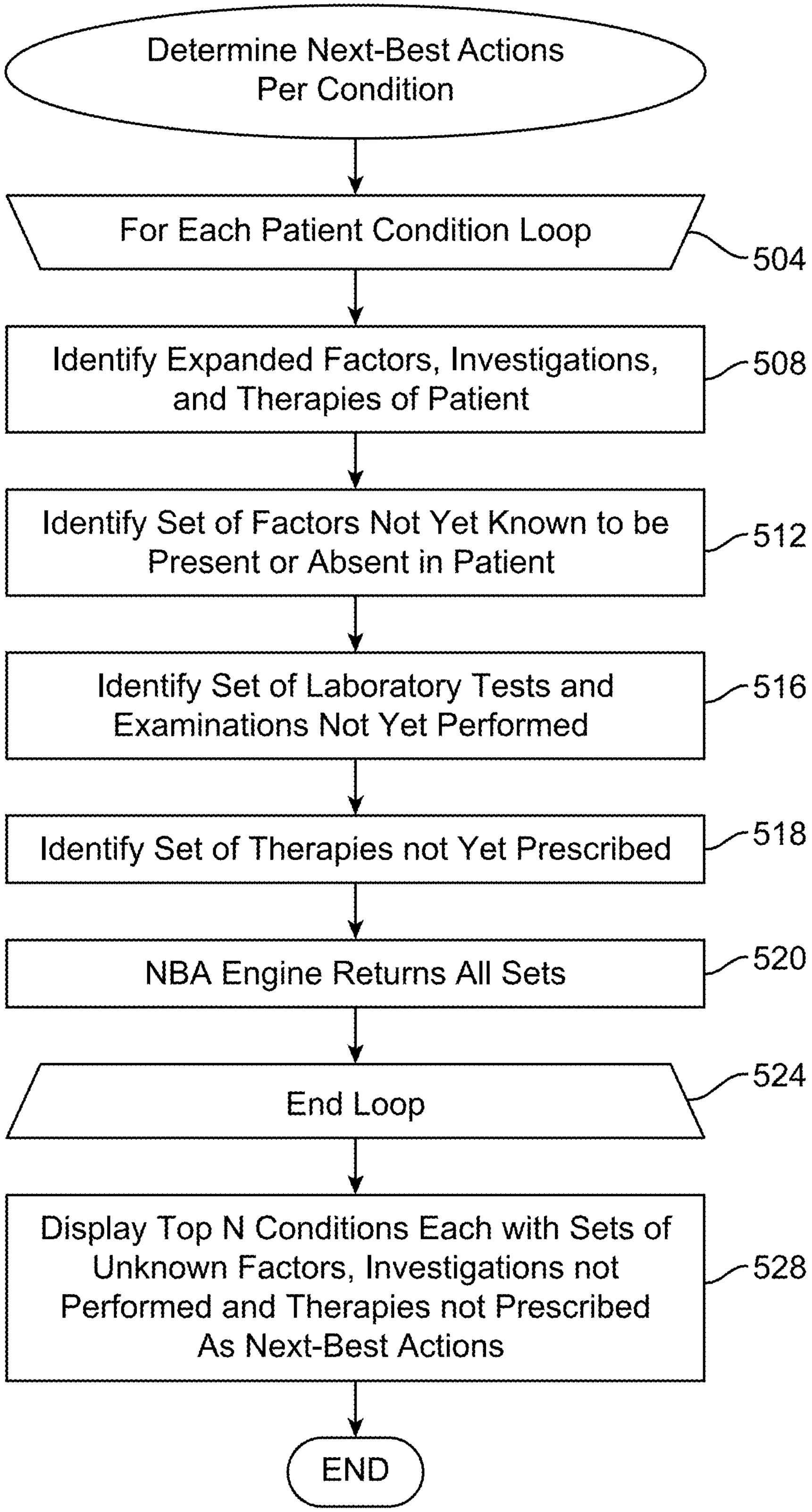
FIG. 15 is a flow diagram for determine next-best actions per medical condition.

FIG. 15 is a flow diagram describing how the next-best actions per condition are determined based upon the patient's current state. Use of the knowledge graph 50 allows the patient's current clinical state to be compared to a body of medical evidence that has been extracted from evidence sources in order to determine next-best actions.

Preferably, the flow diagram of FIG. 14 has been executed and the patient's current clinical state is known: his or her likely conditions, the patient's current diagnostic and risk factors, results from laboratory tests and examinations that have been performed, and any drug or nondrug therapies that the patient has taken, that have been performed upon the patient, or that the patient has undergone. These factors, investigations and therapies preferably have also been expanded as discussed in step 420 to include other factors, investigations and therapies that may be inferred. Alternatively, it is also possible to input a current patient clinical state (i.e., likely conditions, current factors, investigation results and therapies) using other techniques in order to match this state to nodes within the knowledge graph 50.

In step 504 a loop begins for each current condition of the patient with a greater than de minimis probability (identified in step 432 or otherwise), e.g., the top N conditions. Typically, any condition with a probability greater than about 10% will be processed. This minimum is configurable.

In step 508 NBA engine 70 identifies the set of all of the expanded diagnostic and risk factors known to be present or absent, all expanded investigations known to have been performed, and all current and past therapies that the patient has had prescribed, has taken, has undergone, etc., i.e., all those identified in step 420 and 424—all EDF, EDI and ETI nodes in the knowledge graph 50. As mentioned above, these nodes may be identified using an alternative technique and not necessarily from steps 420 and 424. For example, if the patient had presented with a fever and fever node 310 was matched in step 424, then this node is now identified in step 508; if the patient had a test performed for hemoglobin, then EDI node 330 is identified; if the patient had taken penicillin, then node 303 is identified. Step 508 thus produces an identification of all EDF, EDI and ETI nodes in the knowledge graph that correspond to the patient's current state.

In step 512 the NBA engine identifies the set of all diagnostic factors and risk factors not yet known to be present or absent in the patient. As step 508 has identified all of the EDF nodes within the graph database that are known present or absent within the patient, it is straightforward to identify all of the EDF nodes that are currently unknown to be present or absent in the patient. For example, assuming the current condition is condition 300, the engine traverses downward through all factor groups and identifies all those EDF nodes that have not been matched, e.g., if the patient presented with fever but no information is provided regarding nausea, it is unknown whether nausea is present or absent and therefore EDF node 312 will be identified in this step.

Similarly, in step 516 the NBA engine identifies the set of all laboratory tests and examinations that have not yet been performed. Assuming the current condition is condition 300, the engine traverses downward through all investigation groups and identifies all of those EDI nodes that have not been matched, e.g., if the patient had performed hematocrit and hemoglobin tests but nothing else, then EDI node 332 will be identified in this step.

Similarly, in step 518 the NBA engine identifies the set of all therapeutic interventions that have not yet been prescribed (i.e., all therapies that have not yet been applied to the patient). Assuming the current condition is condition 300, the engine traverses downward through all therapy groups and identifies all of those ETI nodes that have not been matched, e.g., if no information is present in the patient medical history concerning a prescription for penicillin V, then ETI node 303 will be identified in this step. ETI nodes corresponding to any of the therapy types of node 662 may be returned.

Next, in step 520 the NBA engine returns all three sets of unknown factors, not-yet-performed investigations and therapies not yet prescribed for the current condition and holds these results with the current condition until the loop ends. As these sets include identification of the unknown EDFs, unperformed EDIs and non-prescribed ETIs, the data returned for each condition can be as simple as the name of each node or any detailed information found via the node's ontology link.

In step 524 after all patient conditions have been processed the loop ends and the NBA engine may return all sets for all conditions to Co-pilot 24 for display, may provide all sets to patient state service 60 for storage or later processing by another application, or may retain all sets from all conditions for further processing in FIG. 16 below.

In step 528 user interface 24 displays to the clinician these top N conditions each with a set of factors not yet known to be present or absent, a set of investigations not yet performed and a set of not yet prescribed therapeutic interventions as the next-best actions. Preferably, the listing of these next-best actions is in order of their importance to a particular condition, such as by using their ranking value (or calculated weight value) from a factor group, investigation group or therapy group for EDFs, EDIs or ETIs, respectively. This ranking value may be listed explicitly alongside each factor, investigation or therapeutic intervention when displayed or may be implicit in that factors, investigations and therapeutic interventions are listed from top to bottom in order of decreasing importance. The total number of next-best actions displayed may be limited, or the number of EDFs, EDIs and ETIs may each be limited.

Other techniques for displaying this information may also be used. For example, the number of conditions presented may be limited to a specific number of conditions, by using a specified threshold, or they may be ordered by their likelihood as established by Patient State Determiner in step 428. The information may be displayed within Co-pilot 24, within a similar standalone product, or integrated with the EHR system. The unknown factors, unperformed laboratory tests and examinations, and non-prescribed therapeutic interventions may be displayed with an indication as to their particular state. The next-best actions may be presented either per condition or in the aggregate. The presentation of the information by the glass user interface may be textual, graphical, audio, video, a combination of the above or in another appropriate format.

Further, while in one embodiment the output next-best-action factors are listed together, the investigations are listed together and the therapeutic interventions are listed together, in another embodiment all may be listed together and ranked against one another, e.g., the first next-best action may be an unknown factor, the second next-best action may be a therapy, and the third may be a recommended test or examination.

In a simple example, assume the same patient as above; in the follow-up session he mentions an allergy to penicillin V and amoxicillin. In that case, the next-best action will be to try non-penicillins and non-betalactam drugs. Hence, the NBA engine might recommend Macrolides.

As mentioned above, EDFs, EDIs and ETIs have characteristics that differentiate them from the prior art; each is atomic, may be placed in context, is composable, is computational, and may be used horizontally. In this flow we have: atomic (steps 512, 516 and 518 identification happen at most precise concept level); in context (at 508, expansion takes place based on the patient's context); composable (the extracted and expanded concepts at 524 compositionally represent the patient state and also represent the next-best actions); computational (the inherent logic of expansion and identification of different elements follows traversal logic in the graph which is computational); used horizontally (one of the different use cases described).

Determine Next-Best Actions Across Conditions

Figure 16:
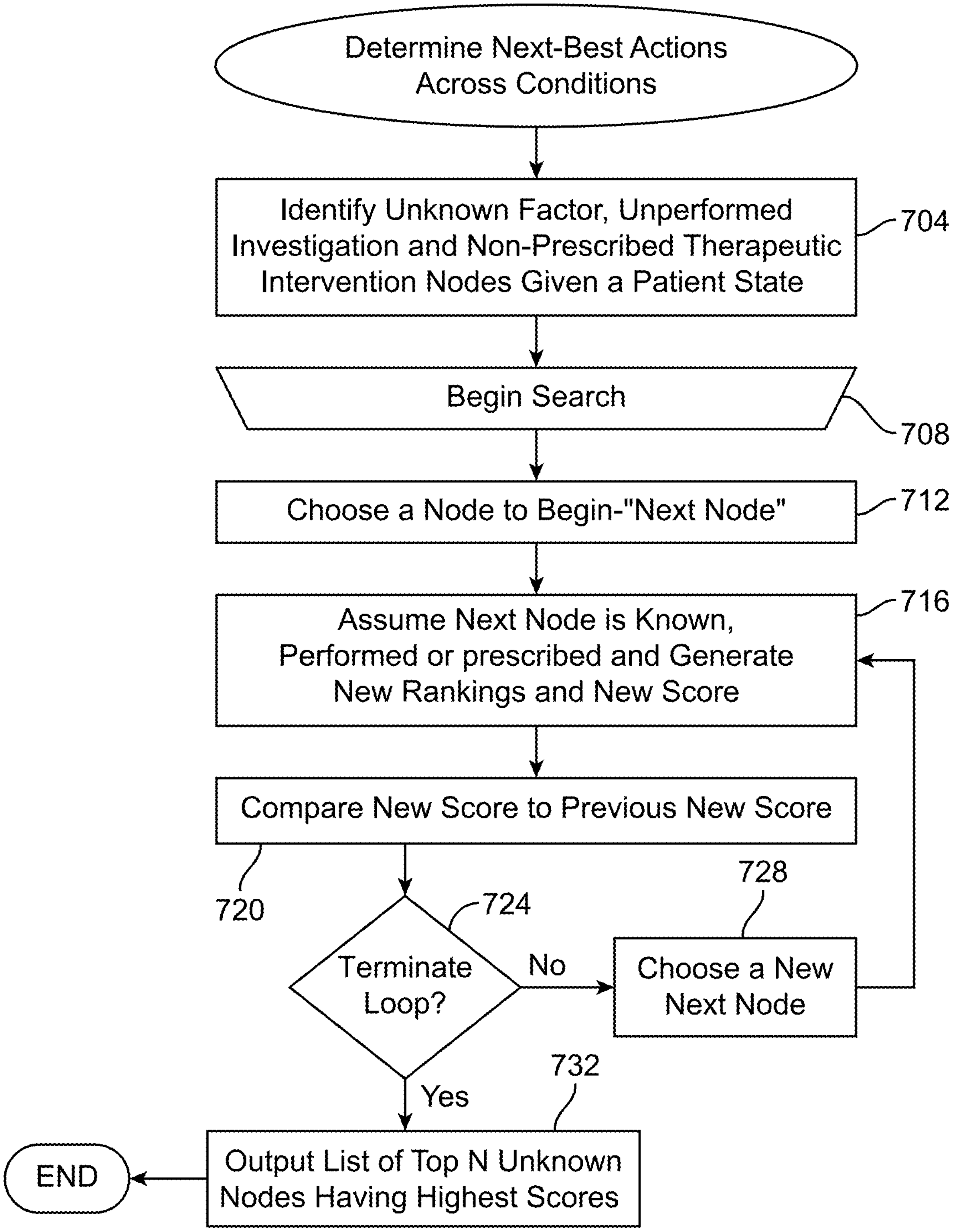
FIG. 16 is a flow diagram for determine next-best actions across medical conditions.

FIG. 16 is a flow diagram describing how the next-best actions across condition are determined based upon the patient's current state. Use of the knowledge graph 50 allows the patient's current clinical state to be compared to a body of medical evidence that has been extracted from evidence sources in order to determine these next-best actions. This flow diagram describes a technique for determining the next-best action across all of the conditions that the patient may have, or a list of the top N next-best-actions. In other words, these next-best actions are the best actions that a clinician can take (e.g., the best diagnostic or risk factor the clinician should ask about, the best laboratory test or examination to perform, or the best therapeutic intervention to prescribe) in order to most quickly diagnose or treat the patient's condition.

If diagnosis is not complete and no medical condition is likely, then the flow below will naturally focus on suggesting questions regarding diagnostic and risk factors and recommending laboratory tests and examinations, although a therapeutic intervention may be recommended if it can help diagnose the condition and no factor or investigation scores highly (also known as diagnosis by treatment). Typically, though, the platform will not suggest therapeutic interventions until the diagnosis is complete or unless the clinician specifically indicates to start suggesting interventions. The clinician can indicate this by updating the patient state in the EHR or by providing input via clinical copilot 24.

On the other hand, if the patient has already been diagnosed then the focus will naturally be on suggesting appropriate therapeutic interventions for that diagnosis. Once the diagnosis is complete (i.e., a medical condition is known), the flow below will cease suggesting next-best actions which are factors or investigations (e.g. it is not logical to suggest tests to confirm diabetes if diabetes has already been confirmed). At this point, the flow may only suggest interventions (and perhaps monitoring) which are ranked depending upon the patient context (i.e., a therapy for a particular medical condition holds its ranking and line of treatment in a therapy group node).

Using the example of FIG. 2 if the patient presents only with a fever this means that the patient has condition 300 or condition 340. The next-best-action will be to ask if the patient has nausea (matching to EDF node 312) and if so, this means that the patient has condition 300, and if not, it is likely the patient has condition 340. Another possibility is to ask the patient to perform a hemoglobin test (assuming EDI node 330 is currently unknown), and if positive, this means that the patient likely has condition 300, while if negative, means the patient likely has condition 340. Thus, a next-best action is determined across, or taking into consideration, any number of medical conditions that the patient may have. Of course, an actual knowledge graph will be much more complex and contain many hundreds of thousands of nodes or more, meaning that an automated search technique is used.

In a first step 704 the current unknown diagnostic or risk factors (i.e., not known to be present or absent), unperformed investigations (i.e., those not yet performed) and nonprescribed therapeutic interventions corresponding to the patient's current state are identified. In addition, their corresponding nodes in the knowledge graph are also identified, i.e., the unknown EDF nodes, unperformed EDI nodes and nonprescribed ETI nodes. Preferably, this step is performed using the results from steps 504-520 of FIG. 15, i.e., those sets of unknown factors nodes, unperformed investigation nodes and nonprescribed therapeutic intervention nodes.

And, although step 704 appears outside of the search loop, it is also possible to identify these unknown, unperformed or nonprescribed nodes during the search loop while the flow is traversing nodes of the knowledge graph. In other words, as the patient's state is known (i.e., the NBA engine knows which factors are known, which investigations have been performed and which therapies have been prescribed), it is also known which nodes are unknown, which are unperformed and which are nonprescribed, and these may be identified as needed in steps 712, 716 and 728.

In step 708 the search loop begins using the knowledge graph and knowing the patient state (i.e., which nodes match with factors, investigations and therapeutic interventions in the patient state and which do not). Any of a wide variety of search algorithms may be used, especially tree search algorithms, and one that has been found to work well is the Monte Carlo tree search. Even a brute force search may work but will take more time and resources.

Next, in step 712 one of the unknown nodes is chosen to begin, the "next node." For example, if it is unknown whether or not the patient has nausea, then EDF node 312 may be chosen to be the first node with which to begin. The next node may also be an EDI node representing an unperformed investigation or an ETI node representing a nonprescribed therapeutic intervention. As mentioned above, if a diagnosis has been reached then this step will not suggest EDFs or EDIs as a next node, only ETIs will be suggested. A diagnosis may be reached when a clinician provides input indicating that a particular medical condition is a diagnosis, may be reached when a medical condition crosses a ranking threshold or a probability threshold (e.g., a medical condition has a probability above 95%), may be reached when the difference between the highest probability and the next highest probability in a differential diagnosis is greater than a certain amount (e.g., one diagnosis is only 80% probable but the next highest is only 35% probable and the certain amount is a 40% difference).

In step 716 given the patient's current state, the search assumes that this next node is now known to be present or known to be absent (e.g., in the case of a factor node, we assume that the patient has responded "yes, I have nausea," or that the clinician has concluded "patient does have nausea") and new condition rankings are generated based upon this new information. This step may be implemented as in steps 420-432 in which the new, now known factor is expanded, these are matched to nodes in the knowledge graph and new rankings of the likely conditions are generated based upon the original patient state plus this new information. If the next node is an investigation node, the search assumes that this investigation has been performed and has a particular result shown in one of the linked EDI result nodes. If the next node is a therapeutic intervention node, the search assumes that this therapeutic intervention has been prescribed for the patient (and the patient has taken, performed or undergone the therapy), e.g., we assume that "the patient has been taking penicillin V." In addition, the search will also generate a search branch and a corresponding score where the assumption for that next node is the opposite, e.g., "patient does not have nausea" (in the case of a diagnostic factor node), "investigation 330 does not have a result given in the range of result node 324" (in the case of an investigation node), or "patient has not been taking penicillin V" (in the case of a therapeutic intervention node).

This step also generates a new score, effectively evaluating how beneficial it is in assuming that the next node is now known in terms of determining the patient's condition; the score represents how effective that assumption is in distinguishing the likely conditions from one another. In one embodiment, the score represents how much the differential diagnoses have changed relative to one another. For instance, if in the patient's original state one diagnosis had a probability of 70% and a second diagnosis had a probability of 75%, but, once the assumption of "patient does have nausea" is made the first diagnosis has a probability of 95% and the second diagnosis now has a probability of 60%, the score for that assumption will be higher. If both diagnoses are now at 70% then the score will be lower. In another embodiment, the score represents how much the probability of the top diagnosis has increased. A score is generated for both the known case and the opposite unknown case.

The score may also represent the success in maximizing the confidence in a potential patient condition using the minimum number of actions (e.g., questions, laboratory tests, therapies applied, etc.). Optionally, the score per action may also take into account the dollar cost of performing the action (asking about a diagnostic factor, performing a laboratory test or examination, administering a therapy), the time involved in performing the action, and the risk of performing the action. How these costs, time and risks are combined to yield a particular score will depend upon the implementation. By way of example, asking about diagnostic or risk factors typically has no cost, little time and no risk, laboratory tests may have minor costs, some time involved and low risk, while some drugs may be quite expensive and may take time, while some nondrug therapies may be less expensive, may take some time but have no risk. More complex examinations (such as an MRI) may have high cost, significant time involved, little risk, but may be very effective in determining a likely condition. These other aspects of a factor, an investigation or therapy (i.e., cost, time and risk) may be held within individual EDFs, EDIs, and ETIs, may be held in their corresponding factor groups, investigation groups and therapy groups, may be held in association with these via the ontology link in each EDF, EDI or ETI, or may be held in a separate database cross-referenced to the individual EDFs, EDIs, ETIs, or in similar manners.

In the case where diagnosis is complete, no differential diagnosis is generated, instead, the score represents the ranking value of the ETI which represents the percentage of time that a particular intervention is used to manage a medical condition. As above, the score may optionally take into account the cost of undergoing the therapy, the time involved and the risk.

In step 720 this generated new score will be stored with reference to the next node (i.e., the unknown node about which the assumption was made) and may be compared to previous scores for previous assumptions made for other unknown nodes. As is known in the art of search algorithms, and especially recursive algorithms such as the Monte Carlo tree search, the search will continue down these two paths, one path assuming nausea and one not (or one path assuming an investigation with a particular result and one not, or one path assuming a therapy has been applied and one not), generating new condition rankings and new scores as it goes. Further, a search algorithm such as the Monte Carlo tree search will also trim (or prune) nodes for which an assumption would be irrelevant, may discard the current search path, and may eventually return to a state where no assumption is made for a next node where an assumption had been made (e.g., EDF node 312 is again unknown) and will make an assumption for another node. In the case where diagnosis is complete, only scores of ETI nodes are compared to one another.

At some point during execution, in step 724 a decision is made to terminate the algorithm. The algorithm may be terminated based upon user input indicating that only a certain number of seconds or fraction thereof should be used in performing the search, based upon only a certain number of levels of recursion that should be used, may be terminated once a particular score threshold has been reached, may be terminated once a particular score is a certain quantity greater than the next largest score, etc. If not terminated, then in step 728 the algorithm chooses a new next node in step 712 from among the unknown, unperformed or nonprescribed nodes identified in step 704 and recursively continues its search by returning to step 716. As known in the art of search algorithms, this next node may rely upon assumptions made for previous unknown nodes or may revert to the original patient state and choose a different unknown node to make an assumption about it.

If the algorithm does terminate, then in step 732 a list is output of the top N unknown, unperformed or nonprescribed nodes having the highest scores from highest to lowest. The nodes may be listed in order with no score or may have the numerical score associated with each one. In other words, since the NBA engine keeps track of the score generated each time a particular unknown node becomes known in step 716, it is able to output this list which may be a single EDF, EDI or ETI node, or multiples of these nodes, thus representing the next-best action or actions across all possible conditions of the patient. The output may simply be the name of the node (e.g., “nausea,” “hematocrit test,” or “penicillin V”), may be preceded by verbiage describing the type of node (e.g., “Ask about this diagnostic factors:,” “Perform this laboratory test:,” or “Prescribed this therapeutic intervention:”), or may include other information found within the node or via it’s ontology link. This output may be delivered electronically to a software application or may be displayed upon a user interface for the clinician. In the case where the diagnosis is complete, only therapies associated with ETI nodes are output.

Once these next-best actions are output, the clinician is thus able to query the patient about an unknown diagnostic or risk factor, able to order a particular laboratory test or examination to be performed, or is able to prescribe a particular drug or nondrug therapy, any of which will result in the best way to reach a diagnosis or effective treatment at that time. Further, once the patient has answered the question, received laboratory or examination results back, or has performed a therapy, this new information may be entered back into the platform in order to execute the flows of FIGS. 14-16 again in order to generate new results, e.g., newly-ranked conditions, new next-best-actions per condition or new next-best actions across conditions.

The output from any of FIG. 14, 15 or 16 may use any suitable user interface and be textual, graphical, in color, a mixture of all these, and it may be implemented as described in U.S. Pat. No. 11,869,674.

Further Embodiments

Any of the method claims listed below may be embodied as an apparatus claim for performing the steps of that method claim that includes a computer system comprising one or more processors and memory that stores instructions, wherein the instructions, when executed by the one or more processors, cause the one or more processors to execute the steps of that method claim.

The invention also includes these further embodiments:

E7. A method as recited in claim 9 further comprising:

identifying all known investigation nodes in said knowledge graph that each represent an investigation performed for said patient, each investigation node being linked to at least said medical condition node in said knowledge graph;

identifying all unperformed investigation nodes in said knowledge graph that each represent an investigation not yet performed for said patient, each unperformed investigation node being linked to at least said medical condition node;

identifying a ranking of each unperformed investigation node that indicates a likelihood that said represented investigation indicates said medical condition, said ranking being stored between said unperformed investigation node and said medical condition node; and outputting said investigations represented by said unperformed investigation nodes in association with said medical condition in order of said ranking of said unperformed investigation nodes.

F2. A method as recited in claim 17 further comprising: displaying the therapy on a user interface.

FF2. A method as recited in claim 25 further comprising: displaying the therapy on a user interface.

Computer System Embodiment

Figure 17A:
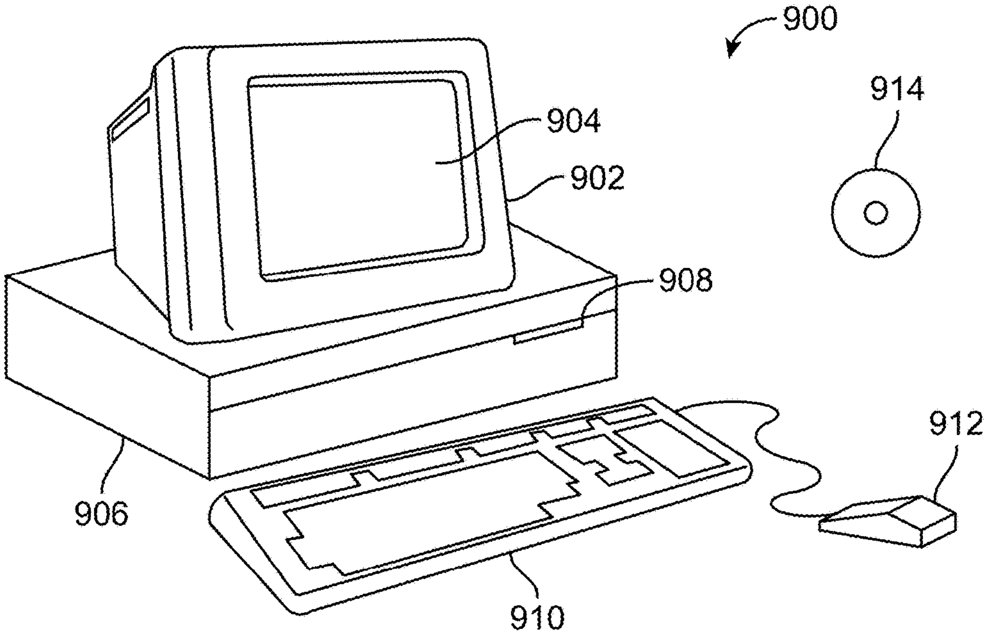
FIGS. 17A and 17B illustrate a computer system suitable for implementing embodiments of the present invention.
Figure 17B:
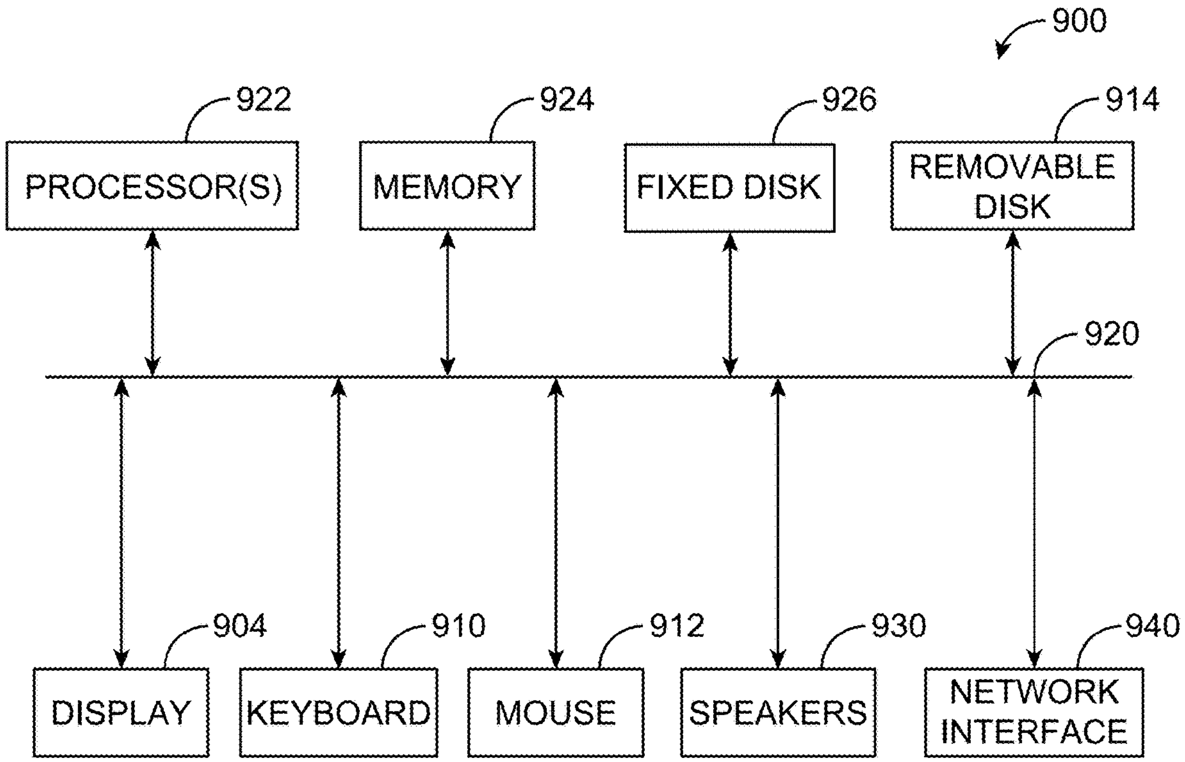

FIGS. 17A and 17B illustrate a computer system 900 suitable for implementing embodiments of the present invention. FIG. 17A shows one possible physical form of the computer system. Of course, the computer system may have many physical forms including an integrated circuit, a printed circuit board, a small handheld device (such as a mobile telephone or PDA), a personal computer or a super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 17B is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary mass storage medium (such as a hard disk, a solid-state drive, a hybrid drive, flash memory, etc.) that can be slower than primary storage but persists data. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those who have skill in the computer software arts. Examples of computer-readable media include, but are not limited to: magnetic media such as hard disks, floppy disks, and magnetic tape; optical media such as CD-ROM s and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher-level code that are executed by a computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

We claim:

1. A method of improving a medical diagnosis when determining a state of a patient across heterogeneous medical ontologies, said method comprising:

receiving a plurality of diagnostic factors known to be present or absent in a patient and a plurality of therapies known to be used or not used by said patient;

matching said diagnostic factors to factor nodes in a knowledge graph and matching said therapies to therapeutic intervention nodes in said knowledge graph, said knowledge graph including a plurality of medical condition nodes linked to said factor nodes and to said therapeutic intervention nodes, wherein at least one of said factor nodes stores an ontology link to an entry in a diagnostic medical ontology that defines a diagnostic factor, wherein at least one of said therapeutic intervention nodes stores an ontology link to an entry in an intervention medical ontology that defines a therapy, and wherein said diagnostic and intervention medical ontologies are different from one another and are traversable from said knowledge graph;

collecting a diagnostic ranking value from along a path from said each matched diagnostic factor node to its linked medical condition node, said each diagnostic ranking value being indicative of the likelihood of a medical condition represented by said each medical condition node, and collecting a therapeutic ranking value from along a path from said each matched therapeutic intervention node to its linked medical condition node, said each therapeutic ranking value being indicative of the likelihood of a therapy of said each matched therapeutic intervention node being used to treat a medical condition represented by said each medical condition node;

combining all collected rank values for each linked medical condition node to produce a final ranking value for said each linked medical condition node; and outputting said medical condition representing said each medical condition node based upon said final ranking value of said each medical condition node.

2. A method as recited in claim 1 further comprising: outputting in association with each of said output medical conditions its corresponding final ranking value.

3. A method as recited in claim 1 further comprising: outputting said output medical conditions in order of final ranking value.

4. A method as recited in claim 1 further comprising:
receiving patient medical history of said patient; and
extracting said diagnostic factors and said therapies from said patient medical history using natural language processing (NLP).

5. A method as recited in claim 1 further comprising:
for at least one of said matched therapeutic intervention nodes, traversing said intervention medical ontology from said one of said matched therapeutic intervention nodes to infer one other therapy known to be used or not used by said patient and matching this other therapy to a therapeutic intervention node in said knowledge graph.

6. A method as recited in claim 1 wherein a node of said knowledge graph located between one of said matched therapeutic intervention nodes and its corresponding linked medical condition node includes demographics of people who use a therapy represented by said one of said matched therapeutic intervention nodes to treat a medical condition represented by said corresponding linked medical condition node.

7. A method as recited in claim 1 wherein each of said therapeutic intervention nodes does not include information specific to a medical condition.

8. A method as recited in claim 1 further comprising:
receiving a plurality of investigations known to be performed or not performed by said patient;
matching said investigations to investigation nodes in said knowledge graph, said medical condition nodes also being linked to said investigation nodes; and
for each of a plurality of said medical condition nodes, collecting a ranking value from along a path between said each medical condition node and each matched investigation node.

9. A method as recited in claim 1 wherein said matching of said diagnostic factors to said factor nodes includes traversing electronically to said diagnostic medical ontology using said ontology link of at least one of said factor nodes, and wherein said matching of said therapies to said therapeutic intervention nodes includes traversing electronically to said intervention medical ontology using said ontology link of at least one of said therapeutic intervention nodes.

10. A method as recited in claim 1 wherein said matching includes traversing at least one of said ontology links in order to disambiguate concepts extracted from said diagnostic factors or said therapies that share a common name but differ in meaning.

11. A method as recited in claim 1 wherein for at least one of said matched diagnostic factors or for at least one of said matched therapies, said matching further comprises traversing the corresponding ontology link into said diagnostic or intervention medical ontology and adding to said matched diagnostic factors or said matched therapies one or more additional concepts that are ancestors or descendants of said matched diagnostic factor or said matched therapy in said diagnostic or intervention medical ontology.

12. A computer system for improving a medical diagnosis when determining a state of a patient across heterogeneous medical ontologies, said computer system comprising:
one or more processors; and
memory storing computer code that, when executed by said one or more processors, causes said computer system to perform operations comprising:
receiving a plurality of diagnostic factors known to be present or absent in a patient and a plurality of therapies known to be used or not used by said patient;
matching said diagnostic factors to factor nodes in a knowledge graph and matching said therapies to therapeutic intervention nodes in said knowledge graph, said knowledge graph including a plurality of medical condition nodes linked to said factor nodes and to said therapeutic intervention nodes, wherein at least one of said factor nodes stores an ontology link to an entry in a diagnostic medical ontology that defines a diagnostic factor, wherein at least one of said therapeutic intervention nodes stores an ontology link to an entry in an intervention medical ontology that defines a therapy, and wherein said diagnostic and intervention medical ontologies are different from one another and are traversable from said knowledge graph;
collecting a diagnostic ranking value from along a path from said each matched diagnostic factor node to its linked medical condition node, said each diagnostic ranking value being indicative of the likelihood of a medical condition represented by said each medical condition node, and collecting a therapeutic ranking value from along a path from said each matched therapeutic intervention node to its linked medical condition node, said each therapeutic ranking value being indicative of the likelihood of a therapy of said each matched therapeutic intervention node being used to treat a medical condition represented by said each medical condition node;
combining all collected rank values for each linked medical condition node to produce a final ranking value for said each linked medical condition node; and
outputting said medical condition representing said each medical condition node based upon said final ranking value of said each medical condition node.

13. A computer system as recited in claim 12 wherein said operations further comprise:
outputting in association with each of said output medical conditions its corresponding final ranking value.

14. A computer system as recited in claim 12 wherein said operations further comprise:
outputting said output medical conditions in order of final ranking value.

15. A computer system as recited in claim 12 wherein said operations further comprise:
receiving patient medical history of said patient; and
extracting said diagnostic factors and said therapies from said patient medical history using natural language processing (NLP).

16. A computer system as recited in claim 12 wherein said operations further comprise:
for at least one of said matched therapeutic intervention nodes, traversing said intervention medical ontology from said one of said matched therapeutic intervention nodes to infer one other therapy known to be used or not used by said patient and matching this other therapy to a therapeutic intervention node in said knowledge graph.

17. A computer system as recited in claim 12 wherein a node of said knowledge graph located between one of said matched therapeutic intervention nodes and its corresponding linked medical condition node includes demographics of people who use a therapy represented by said one of said matched therapeutic intervention nodes to treat a medical condition represented by said corresponding linked medical condition node.

18. A computer system as recited in claim 12 wherein each of said therapeutic intervention nodes does not include information specific to a medical condition.

19. A computer system as recited in claim 12 wherein said operations further comprise:

receiving a plurality of investigations known to be performed or not performed by said patient;

matching said investigations to investigation nodes in said knowledge graph, said medical condition nodes also being linked to said investigation nodes; and for each of a plurality of said medical condition nodes, collecting a ranking value from along a path between said each medical condition node and each matched investigation node.

20. A computer system as recited in claim 12 wherein said matching of said diagnostic factors to said factor nodes includes traversing electronically to said diagnostic medical ontology using said ontology link of at least one of said factor nodes, and wherein said matching of said therapies to said therapeutic intervention nodes includes traversing electronically to said intervention medical ontology using said ontology link of at least one of said therapeutic intervention nodes.

21. A computer system as recited in claim 12 wherein said matching includes traversing at least one of said ontology links in order to disambiguate concepts extracted from said diagnostic factors or said therapies that share a common name but differ in meaning.

22. A computer system as recited in claim 12 wherein for at least one of said matched diagnostic factors or for at least one of said matched therapies, said matching further comprises traversing the corresponding ontology link into said diagnostic or intervention medical ontology and adding to said matched diagnostic factors or said matched therapies one or more additional concepts that are ancestors or descendants of said matched diagnostic factor or said matched therapy in said diagnostic or intervention medical ontology.

* * * * *